(12) United States Patent
Mallapragada et al.

(10) Patent No.: US 6,676,675 B2
(45) Date of Patent: Jan. 13, 2004

(54) PATTERNED SUBSTRATES AND METHODS FOR NERVE REGENERATION

(75) Inventors: Surya K. Mallapragada, Ames, IA (US); Carole Heath, Seattle, WA (US); Howard Shanks, Ames, IA (US); Cheryl A. Miller, Irvine, CA (US); Srdija Jeftinija, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 122 days.

(21) Appl. No.: 09/837,303

(22) Filed: Apr. 19, 2001

(65) Prior Publication Data

US 2002/0051806 A1 May 2, 2002

Related U.S. Application Data

(60) Provisional application No. 60/198,370, filed on Apr. 19, 2000.

(51) Int. Cl.⁷ .............................................. A61B 17/04
(52) U.S. Cl. ...................................................... 606/152
(58) Field of Search ......................................... 606/152

(56) References Cited

U.S. PATENT DOCUMENTS

| | | | |
|---|---|---|---|
| 5,324,591 A | * 6/1994 | Georger et al. | 428/552 |
| 5,358,475 A | 10/1994 | Mares et al. | |
| 5,510,628 A | 4/1996 | Georger, Jr. et al. | |
| 5,735,863 A | 4/1998 | Della Valle et al. | |
| 5,843,156 A | * 12/1998 | Slepian et al. | 128/898 |
| 5,925,053 A | 7/1999 | Hadlock et al. | |

OTHER PUBLICATIONS

Clark, et al. Topographical control of cell behaviour: II. multiple grooved substrata. Development. 1990, vol. 108, pp. 635–644.

Saneinejad, et al. "Patterned glass surfaces direct cell adhesion and process outgrowth of primary neurons of the central nervous system." J. Biomed. Mater. res. 1998, vol. 42, pp. 13–19.

Britland, et al. "Embryonic Xenopus neurites and respond to simultaneous electrical and adhesive guidance cues." Experimental Cell Research. 1996, vol. 225, pp. 31–38.

Tai, et al. "Neurite outgrowth and growth cone morpholoy on micropatterned surfaces." Biotechnol. Prog. 1998, vol. 14, pp. 364–370.

Notification of Transmittal of the International Search Report dated Aug. 14, 2001.

C. Heath, et al.—"The development of bioartificial nerve grafts for peripheral–nerve regeneration", Reviews, Trends Biotechnol Apr. 1998, 16(4), pp. 163–168.

James L. Salzer—"Mechanisms of adhesion between axons and glial cells", The Axon, vol. 8, pp. 164–184.

B.H. Gahwiler—"Organotypic Monolayer Cultures Of Nervous Tissue", Journal of Neuroscience Methods, 4 (1981) pp. 329–342.

Marc Tessier–Lavigne—"Axon guidance by diffusible repellants and attractants"; Curr. Opin. Genet Dev. Aug. 1994, 4(4), pp. 596–601.

(List continued on next page.)

*Primary Examiner*—Gary Jackson
(74) *Attorney, Agent, or Firm*—Dickstein Shapiro Morin & Oshinsky LLP

(57) ABSTRACT

Micropatterned substrates and methods for fabrication of artificial nerve regeneration conduits and methods for regenerating nerves are provided. Guidance compounds or cells are seeded in grooves formed on the patterned substrate. The substrates may also be provided with electrodes to provide electrical guidance cues to the regenerating nerve. The micropatterned substrates give physical, chemical, cellular and/or electrical guidance cues to promote nerve regeneration at the cellular level.

75 Claims, 13 Drawing Sheets

OTHER PUBLICATIONS

Naomi Kleitman, et al. —"The Schwann cell: Morphology and development", The Axon: Structure, Function and Pathophysiology, (1995), vol. 5, pp. 97–115.

Claes–Henric Berthold, et al.—"Morphology of normal peripheral axons"; The Axon: Structure, Function, and Pathophysiology, (1995), vol. 2, pp. 13–48.

J. Lynn Rutkowski, et al.—"Purification and expansion of human Schwann cells in vitro", Nature Medicine, vol. 1, No. 1, Jan. 1995, pp. 80–83.

Gerard J. Tortor—Principles of Human Anatomy, Nervous System, Sixth Edition, (1992) Chapter 16, "Nervous Tissue", pp. 456–468.

Thomas B. Ducker—"Pathophysiology Of Peripheral Nerve Trauma"; Management of Peripheral Nerve Problems, vol. 29, (1980), pp. 475–506.

Lawrence R. Williams, et al.—"Modification of Fibrin Matrix Formation In Situ Enhances Nerve Regeneration in Silicone Chambers"; The Journal of Comparative Neurology 231 (1985), pp. 209–220.

James A. Hammarback, et al.—"Growth Cone Guidance by Substrate–Bound Laminin Pathways Is Correlated with Neuron–to–Pathway Adhesivity", Developmental Biology, vol. 126, pp. 29–39 (1988).

P. Clark, et al.—"Cell guidance by ultrafine topography in vitro", Journal of Cell Science 99, (1991), pp. 73–77.

Peter Clark, et al.—"Growth cone guidance and neuron morphology on micropatterned laminin surfaces", Journal of Cell Science 105, (1993), pp. 203–212.

N. Dubey, et al.—"Development and Characterization Of Magnetically Oriented Collagen Rods For Guided Nerve Regeneration", Faseb J., 10, (1996) p. A386, Abstract #2233.

Marston Manthorpe, et al.—"Laminin Promotes Neuritic Regeneration from Cultured Peripheral and Central Neurons", The Journal of Cell Biology, vol. 97, Dec. 1983, pp. 1882–1890.

Richard P. Burge—"Tissue Culture Observations Relevant To The Study of Axon–Schwann Cell Interactions During Peripheral Nerve Development and Repair", J. exp. Biol. 132 (1987), pp. 21–34.

Veronique Guenard, et al.—"Syngeneic Schwann Cells Derived from Adult Nerves Seeded in Semipermeable Guidance Channels Enhance Peripheral Nerve Regeneration", The Journal of Neuroscience, Sep. 1992, 12(9), pp. 3310–3320.

Ravi Bellamkonda, et al.—"Review: Tissue Engineering in the Nervous System", Biotechnology and Bioengineering, vol. 43, (1994), pp. 543–554.

Thomas K. Morrissey, et al.—"Isolation and Functional Characterization of Schwann Cells Derived from Adult Peripheral Nerve", The Journal of Neurosciene, Aug. 1991, 11(8), pp. 2433–2442.

M.R. Feneley, et al.—"The Role of Schwann Cells in the Regeneration of Peripheral Nerve Axons through Muscle Basal Lamina Grafts", Experimental Neurology 114 (1991), pp. 275–285.

Sherry L. Rogers, et al.—"Neurite Extension by Peripheral and Central Nervous System Neuron in Response to Substratum–Bound Fibronectin and Laminin", Developmental Biology 98, (1983), pp. 212–220.

David C. Turner, et al.—"Guidance of Myogenic Cell Migration by Oriented Deposits of Fibronectin" Developmental Biology 95, (1983), pp. 497–504.

Robert Langer, et al.—"Tissue Engineering", Science, vol. 260, May 14, 1993, pp. 920–926.

Hsin–Chien Tai, et al.—"Neurite Outgrowth and Growth Cone Morphology on Micropatterned Surfaces", Biotechnol. Prog. 1998, vol. 14, pp. 364–370.

Lawrence R. Williams, et al.—"Regenerating Axons Are Not Required to induce the Formation of a Schwann Cell Cable in a Silicone Chamber", Experimental Neurology, 1993, vol. 120, pp. 49–59.

W.F.A. den Dunnen, et al.—"Light–microscopic and Electron–microscopic evaluation of short–term nerve regeneration using a biodegradable poly (DL–lactide–$\epsilon$–caprolacton) nerve guide", Journal of Biomedical Materials Research, 1996, vol. 31, pp. 105–115.

Surya K. Mallapragada, et al.—"Multilayered Semicrystalline Polymeric Controlled Release Systems", American Chemical Society, 1998, pp. 176–185.

Anil Gannepali, et al.—"Nanoscale Patterning of Polymer Surfaces Using Atomic Force Microscopy", Polym. Mater. Sci. Eng. Proceed., 78 (1998), pp. 3–4.

Srdija Jeftinija, et al.—"Effect of capsaicin and resiniferatoxin on peptidergic neurons in cultured dorsal root ganglion", Regulatory Peptides, vol. 39, 1992, pp. 123–135.

Veronique Guenard, et al.—"Influence of surface texture of polymeric sheets on peripheral nerve regeneration in a two–compartment guidance system", Biomaterials, vol. 12, Mar. 1991, pp. 259–263.

Ross W. Gundersen—"Response of Sensory Neurites and Growth Cones to Patterned Substrata of Laminin and Fibronectin in Vitro", Developmental Biology, vol. 121, 1987, pp. 423–431.

D.M. Brunette—"Effects of surface topography of implant materials on cell behavior in vitro and in vivo", Nanofabrication and Biosystems: Integrating Materials Science, Engineering and Biology, Chapter 19, (1996), pp. 335–355.

Qing Zhao, et al.—"Rat sciatic nerve regeneration through a micromachined silicon chip", Biomaterials, vol. 18, 1997, pp. 75–80.

Akio Kawana—"Formation of a simple model brain on microfabricated electrode arrays", Nanofabrication and Biosystems: Integrating Materials Science, Engineering and Biology Chapter 15, (1996), pp. 258–275.

Helen M. Buettner—"Microcontrol of neuronal outgrowth", Nanofabrication and Biosystems: Integrating Materials Science, Engineering and Biology, Chapter 17, (1996), pp. 300–315.

* cited by examiner

PATTERNED SUBSTRATES AND METHODS FOR NERVE REGENERATION

This patent application claims the benefit of U.S. provisional patent application serial No. 60/198,370, filed Apr. 19, 2000, entitled PATTERNED CONDUITS AND METHODS FOR NERVE REGENERATION. U.S. provisional patent application serial No. 60/198,370 is hereby incorporated by reference.

The United Sates Government has certain rights in this invention pursuant to Grant Numbers W-7405-Eng-82 and BES 997387 from the Department of Energy and the National Science Foundation, respectively.

FIELD OF THE INVENTION

The field of this invention is medical devices and methods for nerve regeneration.

REFERENCES

Several publications are referenced herein. Full citations for these publications are provided below. The disclosures of these publications are incorporated herein by reference in their entirety, unless otherwise noted.

BACKGROUND OF THE INVENTION

More than 250,000 surgeries are attempted every year to repair damaged nerves. Nerve injuries complicate successful rehabilitation more than any other form of trauma. Painful neuroma formation, often more disabling than its associated sensory deficits, commonly causes major disability. Improvements in the techniques of nerve repair could provide better return of protective sensibility and tactile discrimination, reduce denervation atrophy of muscles, and prevent or minimize pain syndromes.

The nervous system is composed of neurons and glial, or satellite cells. Glial cells include Schwann cells. The neurons carry signals between the brain and the rest of the body, while the Schwann cells provide support for the neurons and enhance the speed of electrical signals. Schwann cells also produce proteins essential for neuron growth (Bunge, 1994; Tortora, 1992). Each neuron has a cell body, an axon, and dendrites. The tip of an axon is the growth cone and is responsible for navigation. Neurons can make multiple contacts with one or more neurons. The organization of the contacts determines the overall function of the nervous system. The axons are surrounded by an insulating layer or myelin sheath formed by the Schwann cells (Tortora, 1992). Injury to the axon that causes the Schwann cells to lose contact with the axons stimulates production of neurotrophic factors such as nerve growth factors. Nerve growth factor (NGF) has been shown to greatly enhance the growth of neurons in culture. With contact, regenerating axons stimulate Schwann cells to proliferate and form a basal lamina of collagen, proteoglycans, and laminin.

When a nerve is severed, a gap is formed between the proximal and distal portions of the injured nerve. In order for the nerve axon to regenerate and reestablish nerve function, it must navigate and bridge the gap. Under the appropriate conditions, e.g., minimal gap length, the proximal end forms neurite growth cones that navigate the gap and enter endoneural tubes on the distal portion. The growth cones sense the extracellular environment and determine the rate and direction of nerve growth. The motion of the axon is responsive to environmental signals provided by other cells that guide the growth cone (Tessier-Lavigne, 1994).

Once the growth cones reach the distal segment, they enter the endoneurial tubes left from the degenerated axons. However, the growth cones and the dendrites on the proximal stump typically grow in many directions and unless the injury is small, the growth cones may never reach the distal segment. The natural ability of the nerve to regenerate is greatly reduced by the disruption of environmental cues resulting from, for example, soft tissue damage, formation of scar tissue, and disruption of the blood supply (Mackinnon and Dellon, 1988; Fawcett and Keynes, 1990, Buettner et al, 1994).

Several techniques have previously been attempted to aid and accelerate the repair of damaged nerves: suturing the severed ends, suturing an allograft or autograft, or regenerating the nerve through a biological or synthetic conduit (Williams et al., 1983; Valentini et al., 1987; Aebischer et al., 1988; Feneley et al., 1991; Calder and Green, 1995).

Autografts and allografts require a segment of a donor nerve acquired from the patient (autograft) or a donor (allograft). The donor nerve segment is removed from another part of the body or a donor and then sutured between the unattached ends at the injury site. Nerve autograft procedures are difficult, expensive, and offer limited success. Often, a second surgical procedure is required and may lead to permanent denervation at the nerve donor site. Allografts typically require the use of immunosuppressive drugs to avoid rejection of donor segments.

Artificial nerve grafts have been used in attempts to avoid the problems associated with autografts and allografts. Artificial grafts do not require nerve tissue from another part of the body or a donor. However, use of artificial nerve grafts has met with only limited success. Axonal regeneration in the peripheral nervous system has only been achieved for graft lengths up to approximately 3 cm in nonhuman primates. There has been little or no success with longer grafts. The previously used artificial nerve grafts were unsuitable for bridging longer gaps between distal and proximal nerve stumps and, therefore, are unsuitable for treating a significant proportion of nerve injuries.

Neurite growth has been aided to a limited extent by fabricating grooves on substrate surfaces (Weiss, 1945; Turner, 1983; Clark et al., 1987; Dow et al., 1987). The grooves employed in these studies were engraved on plastic or quartz substrates. The substrates utilized are unsuitable for implantation in vivo and thus the authors were unable to determine if the grooves could guide neurite growth in an animal. Alignment of neurons using physical guidance cues alone is highly uncertain and difficult to reproduce. For example, the neurites are typically aligned on only part of the substrate and unaligned on other parts and exhibit undesireable axon branching.

Tai et al., 1998 refer to the effects of micropatterned laminin glass surfaces on neurite outgrowth and growth cone morphology. In Tai et al., micropatterns consisting of laminin stripes alternating with glass stripes were formed on glass coverslips. Neuronal cultures were prepared from chicken dorsal root ganglia and seeded on either micropatterned laminin coverslips or on a uniform laminin coated glass surface. While neuronal growth on the micropatterned laminin surface was biased in the direction of the pattern, severe axon branching formed dense axon outgrowth. Thus, while the laminin provided some level of chemical guidance, applicability of the technique was limited. In addition, the glass substrates are unsuitable for implantation into patients.

Biodegradable conduits filled with magnetically aligned collagen rods have also been used in an attempt to provide directional guidance to regenerating neurons. However, this approach does not provide any chemical guidance to regenerating neurons and has had only limited success. The presence of the collagen rods reduces the space available for neuronal outgrowth, constricts growth, does not reduce axonal branching, and limits the natural transport of oxygen, nutrients, and waste products.

SUMMARY OF THE INVENTION

Preferred embodiments of the present invention provide methods and apparatus for regenerating nerves utilizing substrates having a surface containing grooves, as described herein, and chemical, cellular and/or electrical cues (collectively and individually referred to as "guidance factors") provided in the grooves to obtain the desired nerve growth rates and to regain nerve functionality. Especially preferred nerve growth guidance factors include Schwann cells, stem cells and laminin. The combination of the substrates and guidance factors and methods according to the invention results in accelerated neurite elongation rates, excellent neurite alignment along the substrate grooves, and restored nerve functionality.

In a preferred embodiment of the invention, methods and associated apparatus for regenerating severed nerves are provided comprising a substrate having a surface containing one or more substantially linear grooves, wherein said one or more grooves contain one or more guidance factors for nerve regeneration. The substrate is preferably positioned at an end of a severed nerve such that the grooves are substantially coextensive to the severed nerve end and the nerve is allowed to grow into one or more grooves of the substrate. The grooves preferably contain one or more guidance factors for nerve regeneration.

In another preferred embodiment of the invention, the substrate is in the form of a cylinder and the grooves are disposed on the surface of the inner wall of the cylinder. In a further preferred embodiment, the guidance conduit is porous. The conduit is preferably implanted into an animal and sutured to the ends of a severed nerve to achieve directional nerve growth and regeneration.

In particularly preferred embodiments of the invention the substrate is formed from poly(D,L-lactide) or copolymers of lactic and glycolic acids. In a further preferred embodiment, the substrate also comprises nerve growth inhibitors or "negative guidance factors" (e.g., poly(vinyl alcohol)) to direct and limit neuronal growth to the grooves on the surface of the substrate. According to this preferred embodiment of the invention, one or more negative guidance factors are disposed between the grooves on surface of the substrate. The negative guidance factors inhibit neuron growth outside of the grooves and prevent axon branching of the neuronal outgrowth.

In yet another preferred embodiment, at least one electrode is positioned within said one or more grooves. The combination of preferred guidance factors (e.g., Schwann cells, laminin, and stem cells) and electrical signals generated by the electrode provide further stimulation to orient nerve growth along the axis of the grooves.

The above and other characteristics and advantages of the invention can be better understood from an analysis of the following written description and the accompanying drawings, where like reference numbers represent like elements, or may be learned by practice of the invention.

DETAILED DESCRIPTION OF THE PREFERRED EMBODIMENTS

Reference will now be made in detail to the presently preferred embodiments of the invention, which, together with the following examples, serve to explain the principles of the invention.

In accordance with a preferred embodiment of the present invention, micropatterned substrates are formed to provide physical and/or chemical guidance to the growth cone of a severed nerve. The preferred substrates have a surface containing a plurality of substantially linear grooves. The term "substantially linear groove" refers to a groove that approximates a line and preferably does not branch or intersect with itself. The grooves are preferably substantially parallel to each other and contain one or more guidance factors for nerve regeneration. The term "substantially parallel" refers to grooves that extend approximately in the same direction, preferably along the longitudinal axis of the guidance conduits according to the invention and in the same direction as the severed nerve. The substrate is preferably positioned in proximity to a severed end of the nerve such that the grooves are substantially coextensive to the nerve. The term "substantially coextensive" refers to a juxtapositioning, preferably by suturing or other attachment or fixation, so that the groove is aligned with the severed nerve and the groove boundaries are able to contain and guide the growing, regenerating nerve. The growth of the severed nerve is thus facilitated and guided by the substrate grooves.

Preferably, the micropatterned substrates form or are attached to the inner surface of a guidance conduit. The guidance conduit is preferably filled with media and implanted in animal. The term "media" refers to nutrients, growth factors, fluids and other chemical and/or biological materials desirable for supporting neuronal and cellular growth. The media provides a favorable biological environment for promotion of nerve growth within the guidance conduit. A preferred media is dubellco's modified eagle medium (DMEM), although any suitable media may be used.

The term "micropatterned substrate" or "micropatterned film" refers to a substrate or film having a pattern of one or more grooves formed in the surface. In a preferred embodiment, the grooves are arranged such that when the micropatterned substrate or film is disposed within a guidance conduit, the grooves are substantially parallel to the longitudinal orientation of the conduit. The term "groove" refers to a trench or channel, having measurable depth, formed in the surface of the micropatterned substrate or film.

Figure 1:
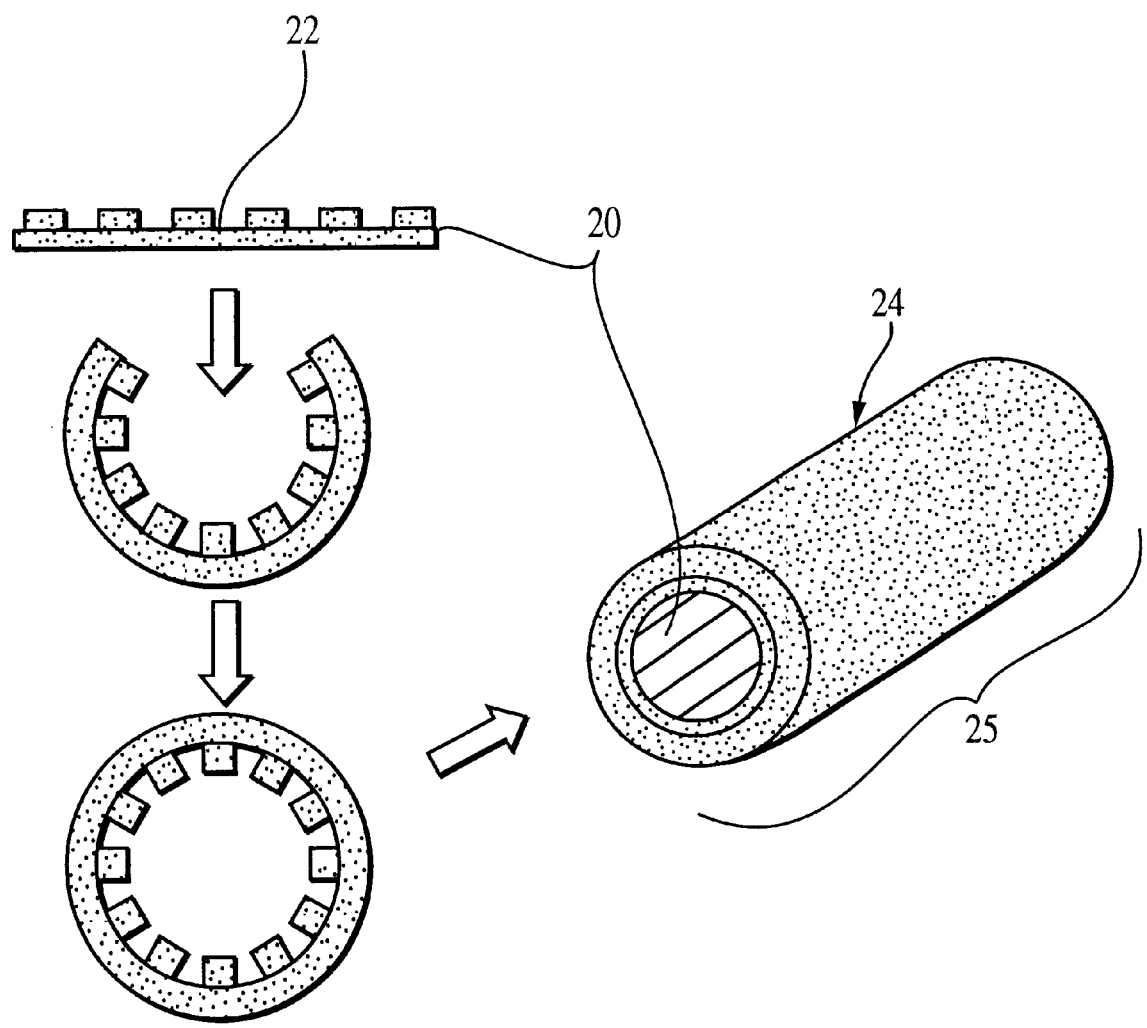
FIG. 1 depicts a biodegradable micropatterned substrate and support conduit in accordance with a preferred embodiment of the invention.

Referring to FIG. 1, a preferred micropatterned substrate 20 is shown. A plurality of grooves 22 are formed in the surface of the micropatterned substrate 20. Grooves 22 are preferably seeded with chemical or other guidance factors, as described in detail below. The resulting micropatterned substrate 20 is preferably placed in a guidance conduit 24 forming nerve regeneration guidance conduit 25 and preferably filled with media to support the growth of neuronal cells. In a preferred embodiment, guidance conduit 24 is porous to allow for supply of nutrients to, and removal of wastes from, the neurons growing in the regeneration guidance conduit 25. The conduit 25 can be surgically implanted in an animal and is preferably sutured at its proximal and distal ends to the respective proximal and distal ends of a severed nerve.

To fabricate an exemplary porous conduit 24, which will support the micropatterned substrate 20 of the invention, poly-D,L-lactide (PDLA) is preferably dissolved in chloroform (about 30% w/v). Sodium chloride crystals are preferably ground, sieved with 120 gauge mesh, and then suspended in the PDLA solution at a concentration of about 75% vol. NaCl/NaCl and PDLA. A pasteur pipette (OD=1 mm) can be dipped into 6% w/v solution of poly(vinyl alcohol) (PVA) in water and allowed to dry. The PVA acts as a release agent. The pipettes are dipped in the polymer/salt suspension, slowly removed, and allowed to dry. This step can be repeated until the outer diameter is about 3 mm. The dry conduits can be placed under vacuum to remove any residual chloroform. The pipettes are placed in water to release the conduit from the support. Water can be replaced every 2 hours until the NaCl is fully dissolved resulting in a conduit 24 with, preferably, about 75% porosity. The resulting exemplary conduits 24 are dried, cut into 1.2 mm sections, and stored in a desiccator at −20° C. until used.

The preferred micropatterned substrate 20 of the present invention contains microscale patterns or grooves 22 formed by any suitable technique, e.g., reactive ion etching (RIE), or atomic force microscopy. The grooves 22 formed in the substrates 20 of the invention provide physical guidance to the regenerating neuronal cells to promote directional growth along the length of the groove 22. In a preferred embodiment of the invention, the grooves 22 are also provided with guidance factors (e.g., Schwann cells, stem cells, laminin, and neurotropic growth factors). The combination of physical and chemical guidance minimizes or eliminates non-directional neuronal growth, i.e., axon branching and neuronal outgrowth in random directions in vivo. The physical and chemical guidance provided by the devices and methods of the invention permits accelerated nerve elongation rates with excellent alignment along the grooves 22 and minimal axonal branching.

Figure 2:
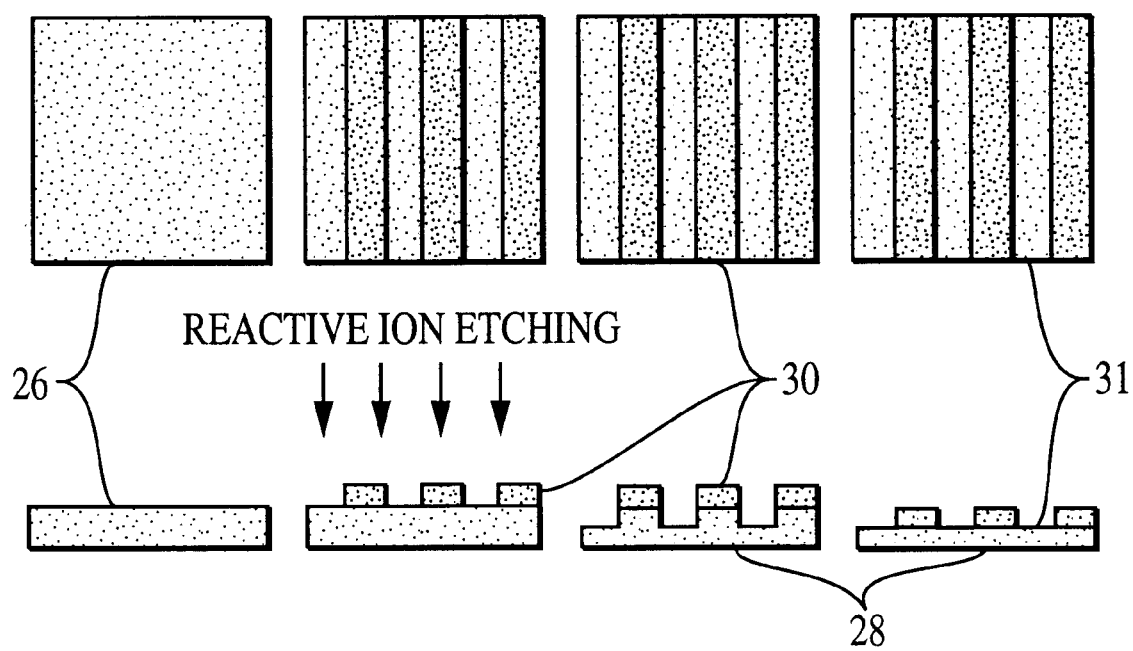
FIG. 2 depicts a top and side view of an exemplary micropatterned die used to form micropatterned substrates according to the invention.

A micropatterned die 28 is typically used as a mold for forming the preferred micropatterned films 20 in accordance with the invention. Dies 28 can be fabricated using, for example, reactive ion etching (RIE) to form grooves 31. Referring to FIG. 2, in a preferred embodiment, a quartz substrate 26 is coated with a mask 30 and subjected to RIE to form micropatterned die 28. The mask 30 is removed to form micropatterned die 28 having grooves 31 with the desired width, spacing, and depth. Any suitable pattern may be used in accordance with teachings of the invention. In a preferred embodiment, the grooves 31 on the dies have, for example, a width of 10 $\mu$m, depth of 4.3 $\mu$m, and spacing of 10 $\mu$m.

Figure 3:
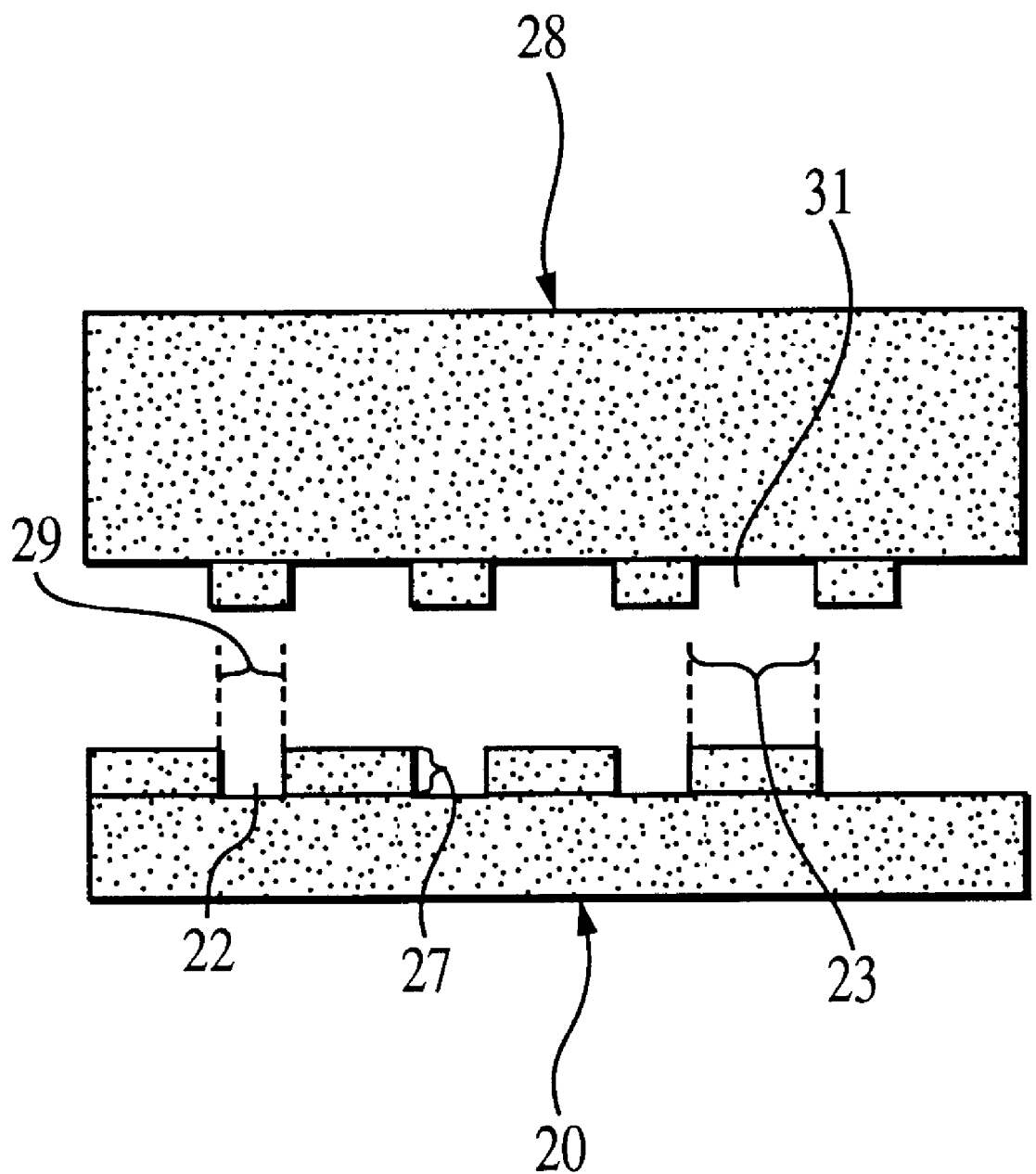
FIG. 3 is an illustration of one relationship between a micropatterned die and a biodegradable micropatterned substrate in accordance with the invention.

Mask 30 is preferably produced with the desired micron or submicron scale patterns using standard lithographic techniques. In a particularly preferred embodiment, a mask 30 is made from chrome and deposited onto a four-inch diameter quartz slide in a vacuum chamber purged with argon at a pressure of less than 1 micro-Torr. The quartz is etched using RIE through the mask 30, leaving behind long rectangular areas capped by chrome. The areas may be of any suitable shape or configuration. After the chrome is removed from the quartz substrate, the quartz substrate can then be used as a die to transfer the micropatterns to a biodegradable polymer by, e.g., heated compression molding between two plates at, for example, about 50° C. for about 10 minutes. The preferred resolution of patterns using this technique are at least about 1.5 $\mu$m. Various micropatterned substrates with various pattern sizes and spacings can be used. The micropatterning of the substrates will ultimately depend on the patterning of the dies. As shown in FIG. 3, a micropatterned die 28 is used to form a micropatterned substrate 20 by any suitable molding technique (e.g., compression molding) resulting in a substrate 20 having the desired groove width 29, groove spacing 23, and groove depth 27.

Preferred materials for the micropatterned substrate 20 include, but are not limited to, poly(D,L-lactide), copolymers of lactic and glycolic acids (PLGA), glycolide trimethylene carbonate, polyester, polyglycolic acid, polyglycolic-acid mesh coated with collagen, collagen, polylactic acid, poly(organo)phosphazine, polyorthoester, copolymers of collagen and glycosaminoglycan, copolymers of L-lactide and $\epsilon$-caprolactone (inner layer), mixtures of polyurethane and polylactic acid (outer layer) and polyimides and polystyrene. Any of the above materials are suitable for use in accordance with the invention. Other suitable film materials can be employed.

Pattern or groove widths 29, as illustrated in FIG. 3, are preferably from about 1 $\mu$m to about 50 $\mu$m wide. The spacing between patterns or grooves is preferably from about 10 to about 100 $\mu$m. It is preferred that grooves of 10 $\mu$m widths and 10 $\mu$m spacings, or 10 $\mu$m widths and 20 $\mu$m spacings, are used. Groove shapes may be of any configuration including, for example, square, circular, triangular, rectangular or irregular. A configuration of substantially parallel grooves is preferred. Optimum groove shape, size and spacing for specific applications can readily be determined by one of ordinary skill in the art given the teachings herein.

In another preferred embodiment, the micropatterned substrate is formed by direct laser etching of PDLA (poly (D,L-lactide)) or PLGA (copolymers of lactic and glycolic acids) coated with poly(vinyl alcohol) (PVA) to selectively etch the PVA film exposing the PDLA underneath. PVA provides a relatively hostile environment for cell adhesion, forcing the neurons and Schwann cells to adhere to the PDLA or PLGA grooves. In other words, PVA is an exemplary negative guidance factor useful for promoting neuronal growth along the more hospitable PDLA or PLGA grooves.

In a preferred embodiment, compression molded films of PDLA (typically having an inherent viscosity of about 0.69 dL/g in chloroform at 30° C.) and copolymers of lactic and glycolic acid (PLGA) with various copolymer ratios such as 85:15, 75:25, or 50:50 are used. The copolymer ratio can be varied in order to control the polymer degradation rate.

In a particularly preferred embodiment, a layer of an adhesive protein such as laminin can be used to coat the surface of the PLGA grooves of a micropaterned substrate promote more rapid nerve regeneration. Direct laser etching allows the proteins to be selectively attached to the PLGA or PDLA grooves because laminin does not adsorb well on PVA. Preferably, laminin is deposited on or over a micropatterned substrate. The liquid laminin is next removed, except for fluid left in the grooves on the substrate. Upon drying, the laminin is concentrated in the grooves of the micropatterned substrate.

Chemical guidance factors are seeded directly on the micropatterned grooves provided in the substrates of the guidance conduits. Guidance factors preferably include neurotrophic factors such as Schwann cells, stem cells, Nerve Growth Factor ("NGF"), laminin, collagen, polylysine, and chicken plasma. In a preferred embodiment, Schwann cells are seeded directly into the grooves formed in the micropatterned substrates. The Schwann cells attach to the grooves. Neurons attach to the regions containing the Schwann cells and align and grow along the grooves.

Schwann cell cultures are preferably isolated from sciatic nerve tissue. In a particularly preferred embodiment, the sciatic nerve is removed from 16–20 day old female Sprague-Dawley rats and placed in chilled Gey's Balanced Salt Solution supplemented with 6.5 mg/ml glucose. The epineurium, connective tissue, and blood vessels is preferably stripped from the tissue using fine forceps, and the nerve can be cut into 1 mm pieces. Chicken plasma (30 mg/ml) with thrombin (2 units/ml) is preferably used to adhere the pieces to tissue culture dishes. Medium containing Dulbecco's Modified Eagles Medium (DMEM) with 10% v/v fetal bovine serum (FBS) and 0.02 mg/ml gentamycin can be changed every two days to feed the cell cultures. The nerve may be transferred onto new dishes weekly until the Schwann cells dissociate from the nerve pieces. The nerve pieces are preferably dissociated and the Schwann cells can be expanded in culture using the previously described medium supplemented with 0.5 $\mu$M isobutylmethylxanthine (IBMX), 5 mM forskolin, and heregulin. Cultures can be determined to be greater than 95% pure by immunocytochemistry staining of S-100 protein. Cell counts are preferably made by trypan blue exclusion with a hemacytometer. The Schwann cells can be injected into a rolled micropatterned substrate conduit 24-hours prior to actual surgical use to allow for sufficient adhesion.

Directional growth and regeneration of severed nerves is achieved by the preferred combination of physical (e.g., grooves) and chemical (e.g., Schwann cells) guidance in accordance with the present invention. The combined effects can be shown using dorsal root ganglia (DRG) as dissociated cell cultures or associated (organotypic) cell cultures. Dissociated cell cultures model individual cell behavior, while organotypic cultures model the behavior of whole cell populations during nerve regeneration.

Variance of the chemical and physical properties of the micropatterned substrates is within the scope of the present invention. In a preferred embodiment, multiple chemical guidance factors are seeded directly in the grooves and groove depth and width are varied for particular applications to achieve optimal results. The use of multiple chemical guidance factors in the grooves can improve cell growth and adhesion. For example, in one experiment the presence of laminin in the grooves improved initial cell adhesion and growth seven-fold. Initial cell counts from six micropatterned film substrates revealed that 1917±113 neuron cells adhered to each of the substrates in the presence of laminin while 264±20 cells adhered to each of the substrates without laminin. Laminin incorporation can result in an almost doubling of axonal extension rates.

In another embodiment, controlled release of nerve growth factor is used to further stimulate directional growth of the nerve growth cone. In addition to laminin, plasma can be used to provide chemical stimulus to the neurons. Chicken plasma stimulated neuron growth. Schwann cells are preferably applied to the grooves at a concentration from about 50,000 cells/cm$^2$ to about 400,000 cells/cm$^2$. Laminin is preferably applied to the grooves at a concentration from about 100 $\mu$g/ml of PBS to about 200 $\mu$g/ml. NGF is optionally provided to the grooves at a concentration of preferably about 1 ng/ml of DMEM (Dulbecco's Modified Eagle Medium) high glucose.

The alignment of regenerating neurons along the axis of the groove is promoted by the physical dimensions of the groove. In accordance with preferred embodiments of the invention, the width, spacing and depth of the grooves can be varied to optimize neuronal growth while limiting axon branching and neuronal outgrowth. Furthermore, grooves serve as an area to deposit guidance factors such as Schwann cells and laminin. The physical guidance provided by the grooves and the chemical or other stimulus provided by the guidance factors further improves the directional growth and alignment of the regenerating neurons along the axis of the groove.

Groove widths for use with Schwann cells are preferably from about 1 to about 20 microns ($\mu$m), more preferably from about 5 to 10 $\mu$m. Groove depths are preferably within the range of from about 1 $\mu$m to about 4 $\mu$m. Groove depths of about 2 $\mu$m or greater are preferred to promote neuronal alignment along the axis of grooves. Groove depths are more preferably from about 3 to about 4 $\mu$m. 100% alignment of the Schwann cells along the grooves can be achieved with groove depths varying, for example, from about 1.4 $\mu$m to about 3.1 $\mu$m.

In a preferred embodiment, the grooves are filled with laminin and Schwann cells, the substrate 20 is rolled up (see FIG. 1) and inserted into a porous hollow guidance conduit 24 (see FIG. 1). In surgical use, the guidance conduit may be sterilized with, for example, ethylene oxide gas prior to implantation in an animal. The guidance conduit, preferably contains media, and the micropatterned substrate containing Schwann cells and other guidance factors seeded in the grooves. The conduit can be implanted in an animal preferably by suturing the regeneration conduit to the proximal and distal nerve stumps on each end of severed nerve. The regeneration conduit remains in the animal for a time sufficient to achieve nerve regeneration and restore functionality to the nerve. The substrate and guidance conduit are preferably biodegradable and resorb within the animal.

An exemplary nerve regeneration process works as follows. A nerve is severed (nerve injury). The severed ends of the nerve are sutured to regeneration conduit formed in accordance with the invention. Fluid accumulates in the cavity within the regeneration conduit between the ends of the injured nerve. As the nerve begins to heal under the influence of the regeneration conduit, a fibrin bridge forms between the proximal and distal ends of the injured nerve. Cells then begin to migrate between the ends of the injured nerve. Finally, the nerve ends reunite and normal neuronal activity may proceed (recovery). Preferably, severed nerves are regenerated over a distance of at least 2–3 cm with at least 70%, more preferably 90%, and most preferably 95% alignment of the neurons along the axis of the groove. The term "alignment" refers to growth of the regenerating neuron along the axis or line of the groove.

In another preferred embodiment, the micropatterned substrates and guidance conduits of the invention are provided in a prefabricated kit form. The kit preferably contains at least one pre-formed substrate. In another preferred embodiment, the kit contains at least one guidance conduit. In yet another preferred embodiment, the kit contains a plurality of guidance factors. The substrates and guidance conduits can be made according to any desired specification. The user or a third-party supplier may also provide the guidance factors. Additionally, the micropatterned substrates and guidance conduits can be provided already in final form with the substrate is inserted into the guidance conduit to form the nerve regeneration conduit.

In a further preferred embodiment, microelectronic circuits (e.g., microelectrodes) can be fabricated on the micropatterned substrates to further enhance nerve regeneration. Electricity can be provided to the regenerating neurons in pulses to further stimulate and orient nerve growth in a particular direction. Neural networks built out of thin-film-transistors (TFT) may optionally be used for guiding nerves. To stimulate local nerve growth, electrical signals can be applied using local, miniature TFT circuits built on flexible silicon or other substrates. The transistors act as local switches to apply electrical pulses to the nerves. FET transistors can be fabricated in the regeneration conduits such that the FET gate areas are exposed to the neurons as they grow. Micropatterned substrates with embedded electrode arrays can be fabricated to stimulate individual neurites in restricted, well-specified locations. The use of physical and chemical guidance cues, as discussed above, can direct the neurites onto the electrodes. Thereby, guidance factors (e.g., chemical, physical, cellular, and electrical) operate cooperatively to promote directional neurite growth.

The use of a combination of chemical, physical, biological, and electrical guidance factors is preferred to regenerate the nerves of the central nervous system (CNS) in vertebrates. The micropatterned substrates are preferably embedded with microelectrodes as discussed above and seeded with neuronal stem cells (NSC) and Schwann cells to achieve functional CNS nerve regeneration.

In a particularly preferred embodiment, micropatterned substrates embedded with microelectrodes are seeded with NSC and Schwann cells to regenerate a severed or damaged optic nerve. A guidance conduit with a micropatterned substrate containing electrodes is implanted in the extracranial part of the optic nerve. Preferably, Schwann cells are pre-seeded in the micropatterned substrates to promote regeneration of NSC in the grooves of tie micropatterned substrate. The resulting regenerated neurons form functional synapses with the neurons in the lateral geniculate nuclei, restoring optic nerve function. The preferred combination of guidance factors, grooves and electrical impulses guide and accelerate the growth of the NSC axons to regenerate optic nerves to transmit signals to the brain.

It is to be understood that the application of the teachings of the present invention to a specific problem or environment will be within the capabilities of one having ordinary skill in the art in light of the teachings contained herein. Examples of the products and methods of the present invention appear in the following examples.

EXAMPLE 1

Film Fabrication

The biodegradable polymers used to construct the micro and nanopatterned substrates of this Example were poly(DL-lactide) and 85/15 poly(DL-lactide-co-glycolide), PDLA and PLGA, respectively. PDLA has a specific gravity of 1.25 g/ml and a glass transition temperature ($T_g$) of 55–60° C.

PLGA's specific gravity is 1.27 g/ml and its $T_g$ is 50–55° C. Both polymers are amorphous, soluble in chloroform and acetone, and have inherent viscosities ranging from 0.55 to 0.75.

Compression molded films of PDLA were obtained by compressing solid PDLA powder in a Carver press at 500 psi pressure at 60° C. for 15 minutes. A solution of PVA in water (20% w/v) was cast over these films for the direct etching studies. PDLA/PLGA films degrade in about 4–6 months depending on the copolymer ratio while PVA films dissolve in about 2 weeks at 37° C.

Solvent cast films were obtained by dissolving three grams of polymer in 10 ml of chloroform making a 30% (w/v) solution. While the PDLA was dissolving, poly(vinyl alcohol) was spun onto the silicon wafer at 4000 rpm for 1 minute (6% PVA is prepared by cooking 6 g PVA/100 ml $H_2O$ for 6 hours at 100° C.). After the PVA dried for 4 hours, PDLA was spun on the wafer at 1800 rpm for 1 minute. The PDLA was allowed to dry for a minimum of 2 hours but 12 hours is preferable. The PDLA film was removed by soaking wafer in water. The thin film of PVA acts as a release agent and the film peels from the wafer with little effort. The films were stored in a desiccator with a drying agent at −20° C. to minimize polymer degradation.

EXAMPLE 2

Quartz Microdie Fabrication

Geometric patterns were formed on quartz glass using a lithographic photomask as a template. The surface of a 2×2×1/16 inch piece of sheet quartz was cleaned in an etching solution. Concentrated sulfuric acid was added to 30% hydrogen peroxide making a 1:1 solution. During the exothermic reaction, the quartz plates were submerged into the solution and etched for 3 minutes. The plates were removed and thoroughly rinsed in DI water.

After the quartz plates were dried, they were placed in the electron beam evaporator for chrome deposition under an ultra-high vacuum. A focused electron beam was used to bombard a cup of metallic chrome with electrons causing the chrome to sublimate and deposit on the surface of the quartz. After 100 nm of chrome was deposited, the plates were removed from the chamber.

The quartz plates were spin-coated with 1512 photoresist and prebaked at 95° C. for 30 minutes. After the plates were cooled, they were exposed to ultra-violet radiation through the photomask. The exposed plates were placed in a commercial photoresist etchant (351 developer) for 1 minute to etch the exposed photoresist. The plates were rinsed in DI water, spun dry and postbaked at 120° C. for 45 minutes to harden the resist.

After the photolithography was complete, the quartz plates covered with patterned photoresist were immersed in CR4 commercial chrome etchant. The chrome that was exposed during photolithography was removed to expose the quartz surface while the photoresist kept the non-exposed chrome from being etched. The photoresist was removed by flowing acetone over the quartz plates and then rinsing the plates with methyl alcohol. The plates were rinsed with DI water and spun dry. The quartz plates were placed in the Reactive Ion Etcher (Plasm Therm 720, dual-chamber, Leybold 360 turbo-pump). The chamber was evacuated and oxygen was admitted at a flow rate of 98 sccm with the oxygen pressure maintained at 80 mTorr. A radio frequency (RF) plasma was created over the plates bombarding the surface with 300 V oxygen ions that clean away any organic residue. The chamber was then pumped out and filled with atmospheric oxygen and $CHF_3$ (Freon 23) with flow rates of 5 sccm and 45 sccm, respectively. The chamber pressure was maintained at 40 mTorr. An RF plasma was formed over the plates creating an ion bombardment voltage of 435 V resulting in an etch rate of 24 nm per minute for the quartz surface. After the quartz was etched, the plates were submerged in CR4 chrome etch to remove the chrome mask. The mesas patterned into the quartz imprinted the grooves onto the polymer films. The silicon wafers used as dies for the solvent cast films were fabricated with the lithographic methods stated above.

EXAMPLE 3

Patterning Microgrooves in Biodegradable Polymer Films

Biodegradable polymer films were patterned with microgrooves by compressing smooth polymer films with a patterned quartz microdie. Smooth films were fabricated, and then imprinted with the microgrooves using the quartz microdie of Example 2.

First, a monolayer of closely packed polymer pellets was arranged on a clean 1×3 inch glass slide. Approximately 10 polymer pellets (cylindrical pellets of 1 mm diameter and 2 mm length) make a 10 mm diameter, 0.5 mm thick film. Another glass slide was placed on top of the pellets and the unit was placed in a press (12-ton hydraulic press, Carver Laboratory Press, IN). The press was closed until the platens were just touching both glass slides and then the platens were heated to 60° C. Since the polymer is amorphous, it softens when it is in contact with the glass but the whole pellet does not melt. Pressure was applied gradually over 15 minutes so the softened polymer filled the space between the pellets forming a smooth defect-free substrate. After 15 minutes, the pressure was increased to 500 psi for 5 minutes. The unit was removed from the press and the smooth films were transferred to a clean petri dish.

Next, a smooth film was placed on the patterned quartz die. A glass slide is placed on top of the smooth film. When the press temperature was ambient temperature, the die unit was placed in the press. The press was closed until the platens just made contact with the glass. When the press temperature reached 50° C., pressure no greater than 50 psi was applied to the unit. Temperature shock and higher pressure can break the quartz die. The unit was heated at 50° C. for 5 minutes at minimal pressure to imprint the microsized pattern on the polymer. The cooled unit was placed into the freezer for about one minute to facilitate removal of the patterned polymer substrate. The patterned substrates were stored in a desiccator over a half pound of anhydrous $CaSO_4$ drying agent DRIERITE® to prevent degradation due to hydrolysis. Since biodegradable polymers are extremely sensitive to and degrade with exposure to heat and humidity, exposure is limited by using the lowest softening temperature, minimizing the duration of the exposure, and storing the polymer in a desiccator.

The nanosized grooves were etched on solvent cast films. One gram of polymer was dissolved in 10 ml of chloroform. Using a microsyringe, one drop of polymer solution was cast on a 5 mm² piece of steam sterilized, glass slidecover. The films were allowed to dry for 48 hours. Laminin was coated on the PDLA surface and allowed to dry. Next, a film of poly(vinyl alcohol) was spun on top of the laminin to provide a surface that does not encourage cell adhesion. Finally, atomic force microscopy (AFM) was used to etch through the top film to expose the laminin, which promotes cell adhesion. The films were stored in a desiccator with a drying agent. The nanosized grooves were etched in the substrate surface with the AFM in contact mode. The AFM tip was microfabricated from silicon nitride and oxide sharpened. The solvent cast film on the glass substrate was mounted and placed on the AFM stage. The tip was fastened onto the E scanner and adjusted so the laser beam was centered on the tip, maximizing the signal to the detector. The tip was lowered near the film surface and engaged. The surface of the film was scanned and a smooth region was chosen to make the nanogrooves. To etch the grooves, the scan size was set to 1.5 µm, the set point is 3 V, the scan rate was increased to 12.2 Hz and the slow scan axis is disabled. The length of the groove was controlled by the scan size, the depth by the scan rate, and the width is 20–30 nm. The grooved films were stored in a desiccator to prevent degradation of the polymer by hydrolysis.

EXAMPLE 4

Seeding Schwann Cells on Substrates

Purified Schwann cells were rinsed with 5 ml of HBSS (3 times for 5 minutes each). The Schwann cells were removed from the flask by placing 10 ml of 0.25% trypsin in HBSS in the flask for about one minute. The solution was removed and the cells were incubated for 10 minutes. After the cells detached from the flask, 9 ml of medium was added to the reconstitute the cells. The cells in 9 ml of media were removed and placed in a centrifuge tube. The cells were centrifuged for 8 minutes at 1000 rpm and the medium was removed. The desired amount of medium was added to the Schwann cells and the medium was mixed with a 1 ml pipette to ensure cell separation. The Schwann cells were fluorescent labeled with SYTO23 with 3.7 µl dye/ml DMEM and incubated at 37° C. for 30 minutes. The Schwann cells were seeded in concentrations of 50,000 to 400,000 cells per square centimeter on the patterned substrates coated with laminin (100–200 µg/ml PBS).

EXAMPLE 5

Groove Width and Spacing Patterns for Cell Alignment

An observational study of various groove width and groove spacing was performed according the following configurations:

| Groove width (µm) | × Groove spacing (µm) |
|---|---|
| 4 | 4 |
| 4 | 20 |
| 4 | 100 |
| 10 | 10 |
| 10 | 20 |
| 20 | 4 |
| 20 | 20 |
| 20 | 100 |

Substrates patterns of 10 µm (width)×10 µm (spacing between grooves) and 10 µm (width)×20 µm (spacing between grooves) were found to provide the optimal Schwann cell and neurite alignment.

EXAMPLE 6

Substrate Adhesion

Improvements in cell adhesion were observed by coating the substrate with laminin. Laminin [100–200 µg/ml PBS]

provided excellent cell adhesion properties. Schwann cells adhered to the PDLA coated with laminin seven times better compared to non-coated PDLA. Adsorbing the laminin to the PDLA surface for 10 minutes and then removing the puddle with a pipette held perpendicular to the surface caused residual solution pooling in the grooves. This increased the laminin concentration in the grooves, which enhanced alignment with the grooves.

EXAMPLE 7

Groove Depth

Various groove depths were used with the substrate patterns. Compression molded substrates with depths of 1.5, 1.8, 1.9, 2.1, 2.3, 3.1, and 3.3 $\mu$m and solvent cast films with depths of 2, 3, and 4 $\mu$m were evaluated for cell alignment using the 10 $\mu$m (width)×10 $\mu$m and 10×20 $\mu$m width/spacing pattern.

Regeneration of dissociated dorsal root ganglia (DRG) was tested using laminin coated substrates having grooves seeded with Schwann cells. The Schwann cells maintained ~100% alignment with the axis of the grooves at all groove depths compared with ~72% alignment on smooth substrates to the chosen major axis. The dissociated DRG were tested on 2, 3 and 4 $\mu$m PDLA films (laminin coated). The results of tests on various groove dimensions were as follows:

10×10×3 $\mu$m 77%±3 DRG aligned with the groove axis

10×20×3 $\mu$m 70%±3 DRG aligned with the groove axis

10×10×4 $\mu$m 92%±3 DRG aligned with the groove axis

10×20×4 $\mu$m 83%±2 DRG aligned with the groove axis

EXAMPLE 8

Substrate/Film Degradation

Compression molded substrates and solvent cast films were analyzed at 1, 2 and 4 weeks for rate of degradation in DMEM (dulbecco's modified eagle media). The compression molded substrates have complete degradation of the mesas after 1 week in media. By 2 weeks in DMEM, the substrate surface was less smooth and beginning to crack. At 3 weeks, the surface was buckling and pitting.

After 1 week in media, the solvent cast films were showing no signs of degradation. At 2 weeks, the mesa edges were slightly rounded but there was no change in the average depth of the grooves. After 4 weeks, the textured surface on the top of the mesas was beginning to degrade and flow into the grooves. The edge of the mesas was continuing to round. At 4 weeks, the average groove depth had decreased by 5%. Substrates/films with laminin adsorbed were monitored to see if the laminin increased the rate of degradation. There was no measurable change due to the laminin but the surface was slightly clouded.

EXAMPLE 9

Neurite Alignment with Substrate Grooves

Figure 7:
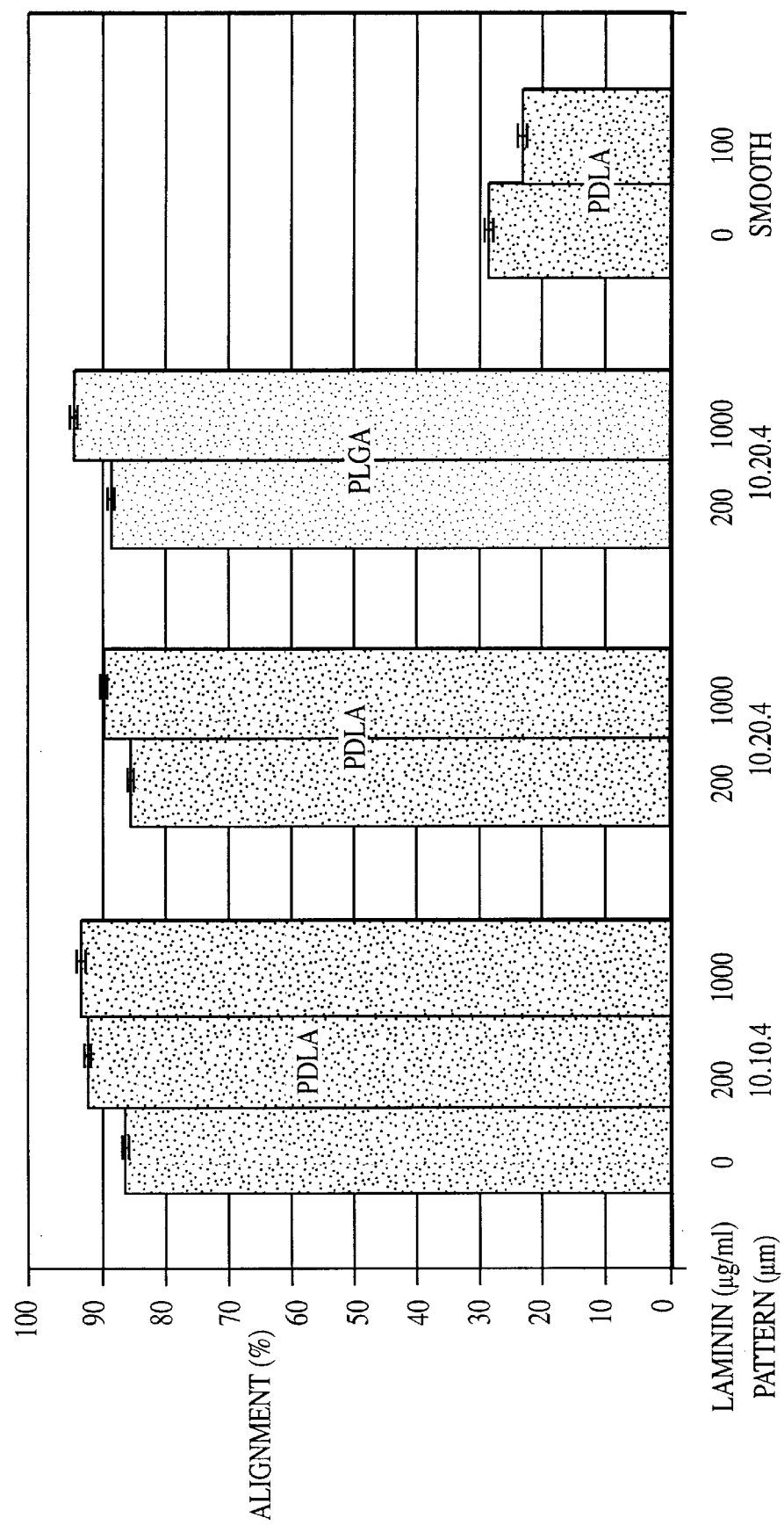
FIGS. 7–11 are charts illustrating the results of experiments on the effects of laminin and micropatterned biodegradable polymers on neurite alignment and elongation.

Increasing laminin concentration improved neurite alignment at a 95% confidence level for 0–200 $\mu$g laminin and 200–1000 $\mu$g laminin, except from 200–1000 $\mu$g laminin on the 10 $\mu$m groove width by 10 $\mu$m groove spacing. These results are illustrated in the chart of FIG. 7. The difference was due to groove spacing where the 'flow effect' of the cells with the grooves was stronger on the narrowly spaced 10 $\mu$m pattern than on the wider 20 $\mu$m spacing where laminin concentration from 200–1000 $\mu$g improved alignment. On smooth substrates, alignment along a preferred axis decreased because of greater neurite outgrowth in random directions.

Figure 8:
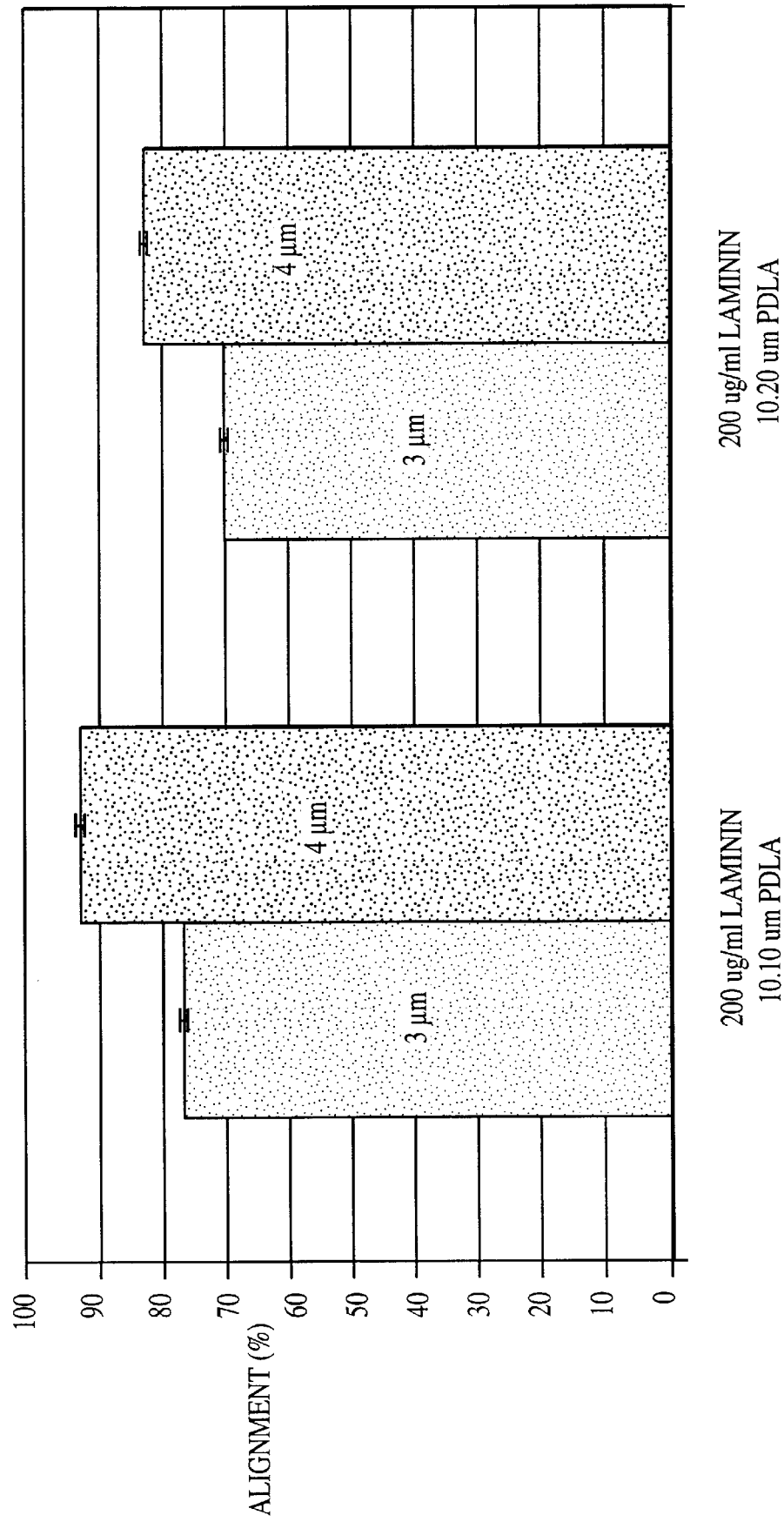

Excellent neurite alignment occurred on films with groove depths of 4 $\mu$m, as illustrated in the chart of FIG. 8, showing that deeper grooves support neurite alignment. Groove spacing of 10 $\mu$m proved excellent for neurite alignment at a 95% confidence level due to the 'flow effects.'

Figure 9:
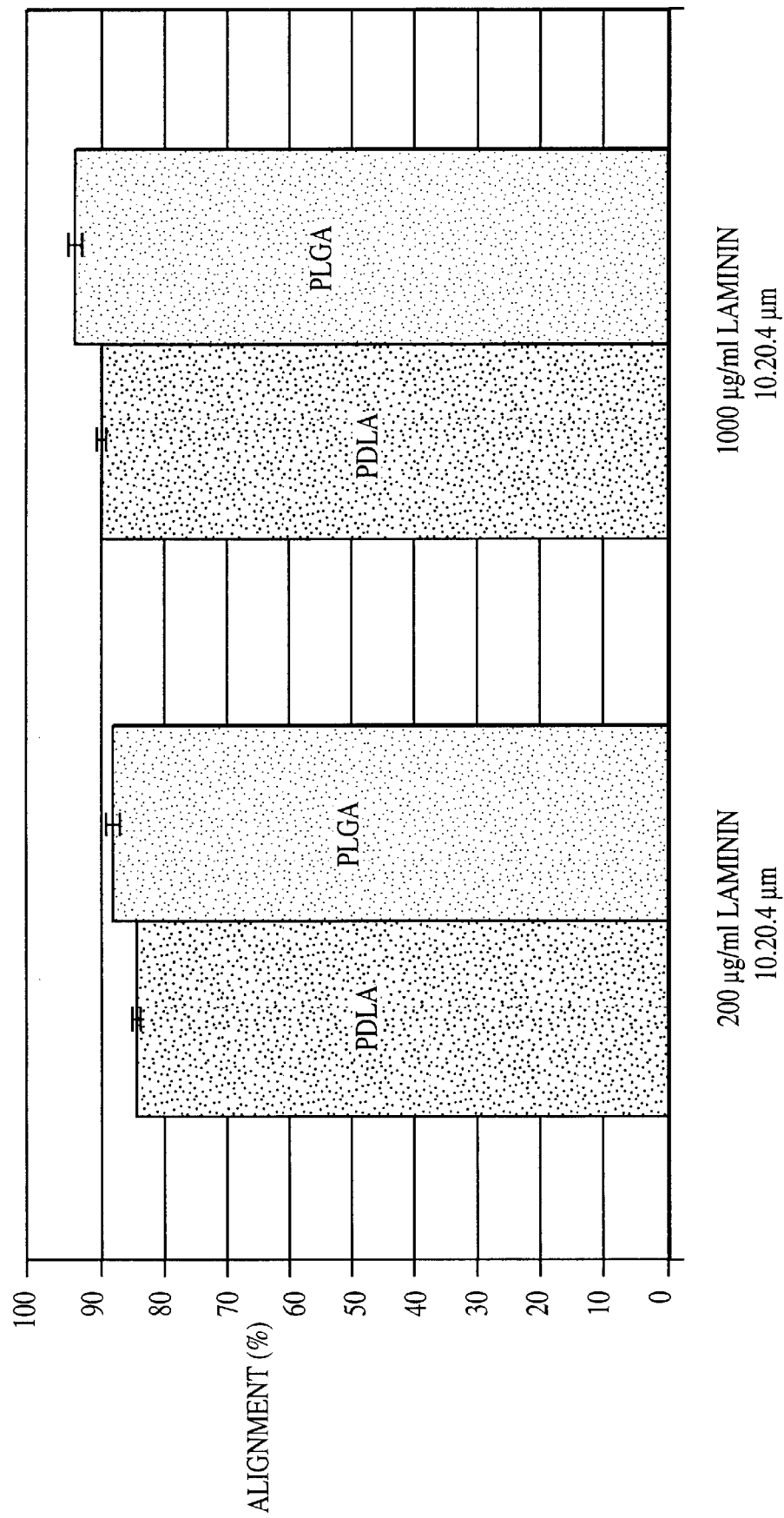
Figure 10:
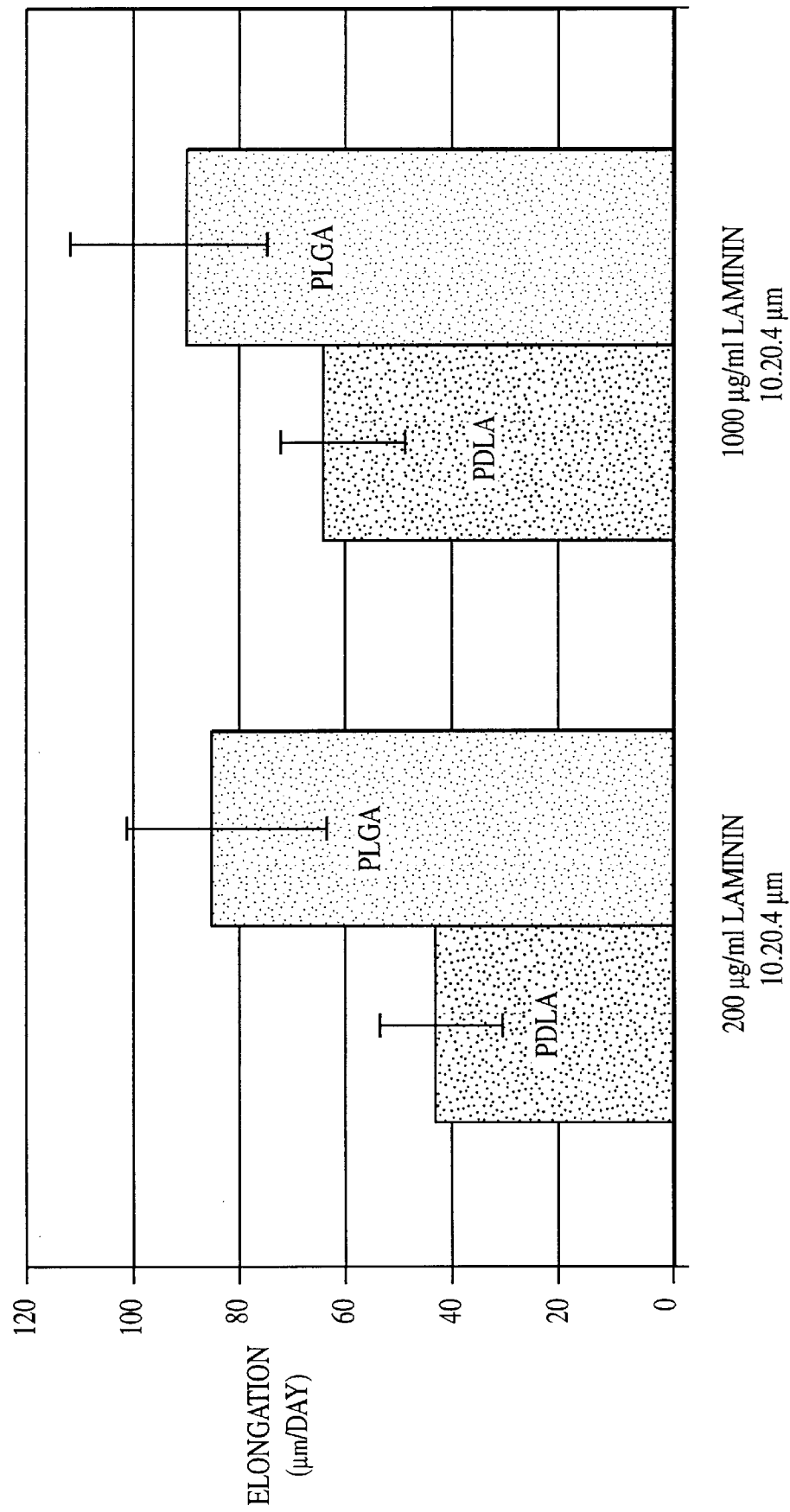

Polymer type affected neurite alignment at a 95% confidence level, as illustrated by the chart of FIG. 9. PLGA improved neurite alignment over PDLA but the mechanism for the difference was not clear. As illustrated by the chart of FIG. 10, polymer type also affected neurite elongation on PLGA coated with 200 $\mu$g laminin at a 80% confidence level. This increase in elongation probably occurred because PLGA was a less hostile environment compared with PDLA. A laminin concentration of 1000 $\mu$g/ml did not improve elongation because PLGA already promoted good growth cone locomotion.

EXAMPLE 10

Conduit Implantation and Measurement of Nerve Regeneration

Figure 13:
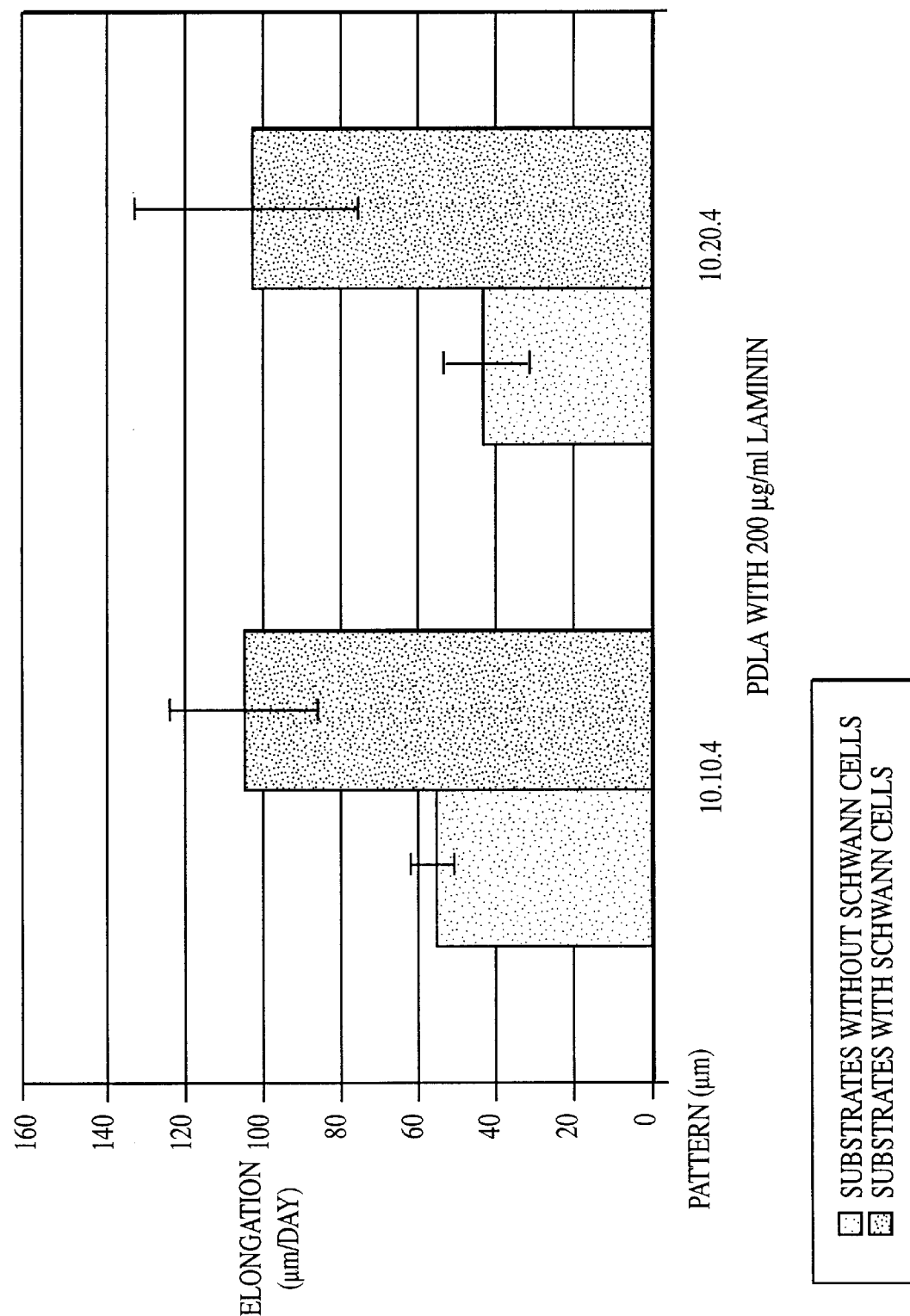

The conduit, prefilled with media and the micropatterned biodegradable substrate containing Schwann cells seeded in the grooves were prepared and sutured to the proximal and distal nerve stumps on each end of a rat severed nerve. After implantation, the muscle compartments were closed with sutures and the rats were monitored for hind limb denervation complications. The conduits were examined after 4, 6, and 8 weeks to determine nerve regeneration rates. The animals were anesthetized as before and killed by intracardiac perfusion with physiological salt solution followed by 4% glutaraldehyde in 0.1 M cacodylate buffer. The conduits were dissected, the tissue fixed for 4 hrs. at room temperature, and the axon extension rates in Vivo were ascertained. The results were studied by light microscopy after sections were stained with toluidine blue and fuchsin. The conduits were examined to check the extent of nerve cable formation after 8 weeks through the conduits. The results of the experiments are shown in FIGS. 10, 11 and 13.

As shown in FIG. 10, the polymer type used to form the substrate influenced the neurite elongation rate. The elongation rate measured in $\mu$m/day using a PLGA substrate was approximately twice that of a PDLA substrate when 200 $\mu$g/ml of laminin was used in the substrate. Increasing the laminin concentration from 200 $\mu$g/ml to 1000 $\mu$g/ml improved the elongation rate for PDLA substrates from approximately 42 to 62 $\mu$m/day.

Figure 11:
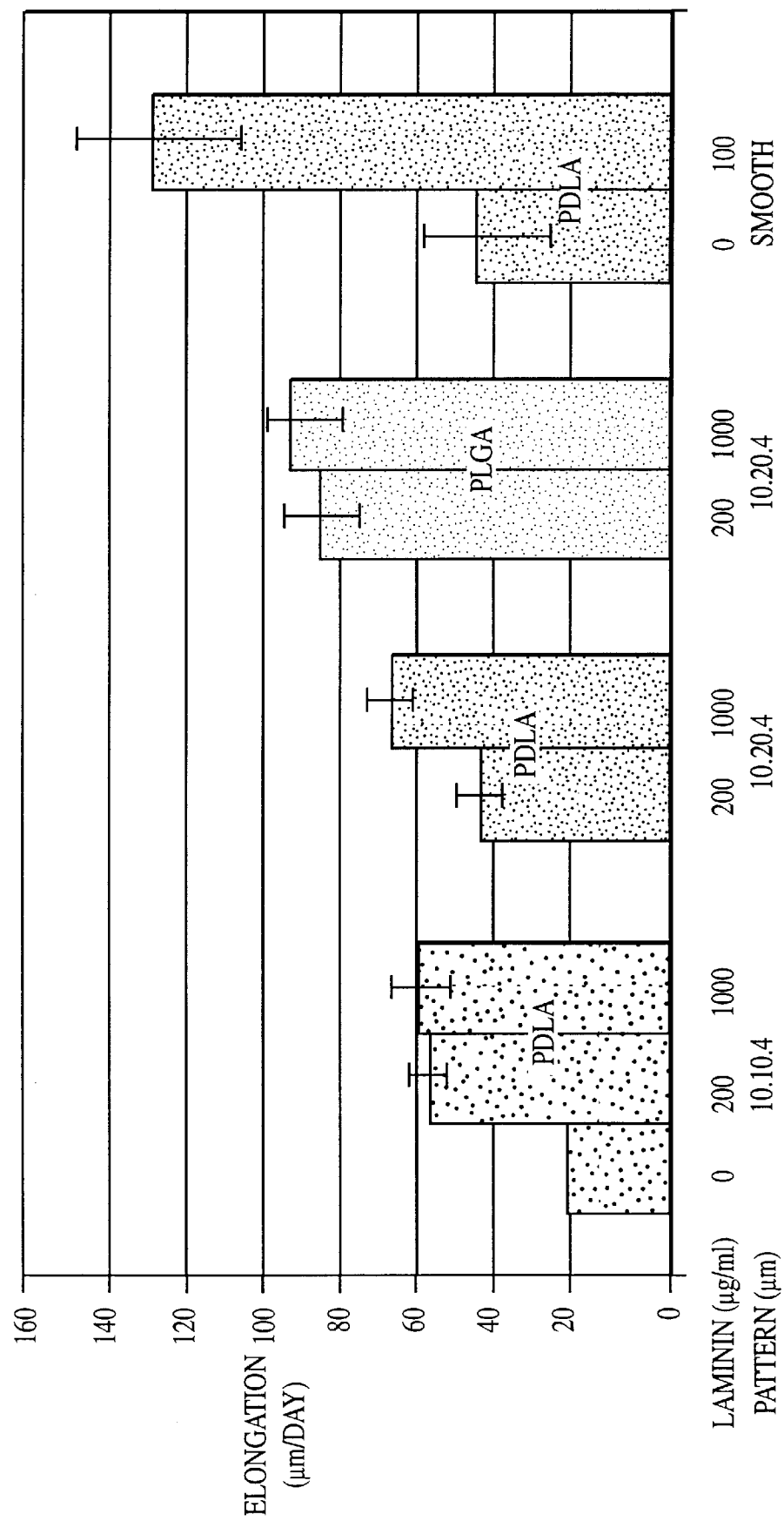

FIG. 11 shows the effects of increasing laminin concentration in PDLA and PLGA substrates using grooves 10 $\mu$m wide×10 $\mu$m spaced×4 $\mu$m deep (10.10.4 groove pattern) and 10 $\mu$m wide×20 $\mu$m spaced×4 $\mu$m deep (10.20.4 groove pattern). Increasing the laminin concentration from 0 to 200 $\mu$g/ml significantly improved the elongation rate in PDLA substrates with 10.10.4 groove patterns (see Table 1 below). However, an increase from 200 $\mu$g/ml to 1000 $\mu$g/ml of laminin did not significantly improve elongation rates in the PDLA substrates with 10.10.4 groove patterns. Increasing the laminin concentration from 200 $\mu$g/ml to 1000 $\mu$g/ml in PDLA substrates with 10.20.4 groove patterns significantly improved the elongation rate as shown in Table 1 below. However, increasing the laminin concentration from 200

μg/ml to 1000 μg/ml in PLGA substrates with 10.20.4 groove patterns did not significantly improve elongation rates.

TABLE 1

Neurite Alignment[a] and Elongation[c] on Solvent Cast Films

| Pattern(μm) | Polymer | Laminin μg/ml | Alignment[a] (%) | Elongation[c] (μm/day) |
|---|---|---|---|---|
| 10 × 10 × 3 | PDLA | 0 | 88 ± 1 | 21 ± 4 |
| 10 × 10 × 3 | PDLA | 200 | 77 ± 1 | — |
| 10 × 20 × 3 | PDLA | 200 | 70 ± 1 | — |
| 10 × 10 × 4 | PDLA | 0 | 86 ± 1 | 21 ± 3 |
| 10 × 10 × 4 | PDLA | 200 | 92 ± 1 | 56 ± 5 |
| 10 × 10 × 4 | PDLA | 1000 | 93 ± 1 | — |
| 10 × 20 × 4 | PDLA | 200 | 84 ± 1 | 43 ± 8 |
| 10 × 20 × 4 | PDLA | 1000 | 90 ± 1 | 64 ± 7 |
| 10 × 20 × 4 | PLGA | 200 | 88 ± 1 | 85 ± 16 |
| 10 × 20 × 4 | PLGA | 1000 | 94 ± 1 | 91 ± 20 |
| Smooth[b] | PLGA | 200 | 36 ± 1 | — |
| Smooth[b] | PDLA | 0 | 28 ± 1 | 42 ± 12 |
| Smooth[b] | PDLA | 100 | 23 ± 1 | 128 ± 27 |

Figure 12:
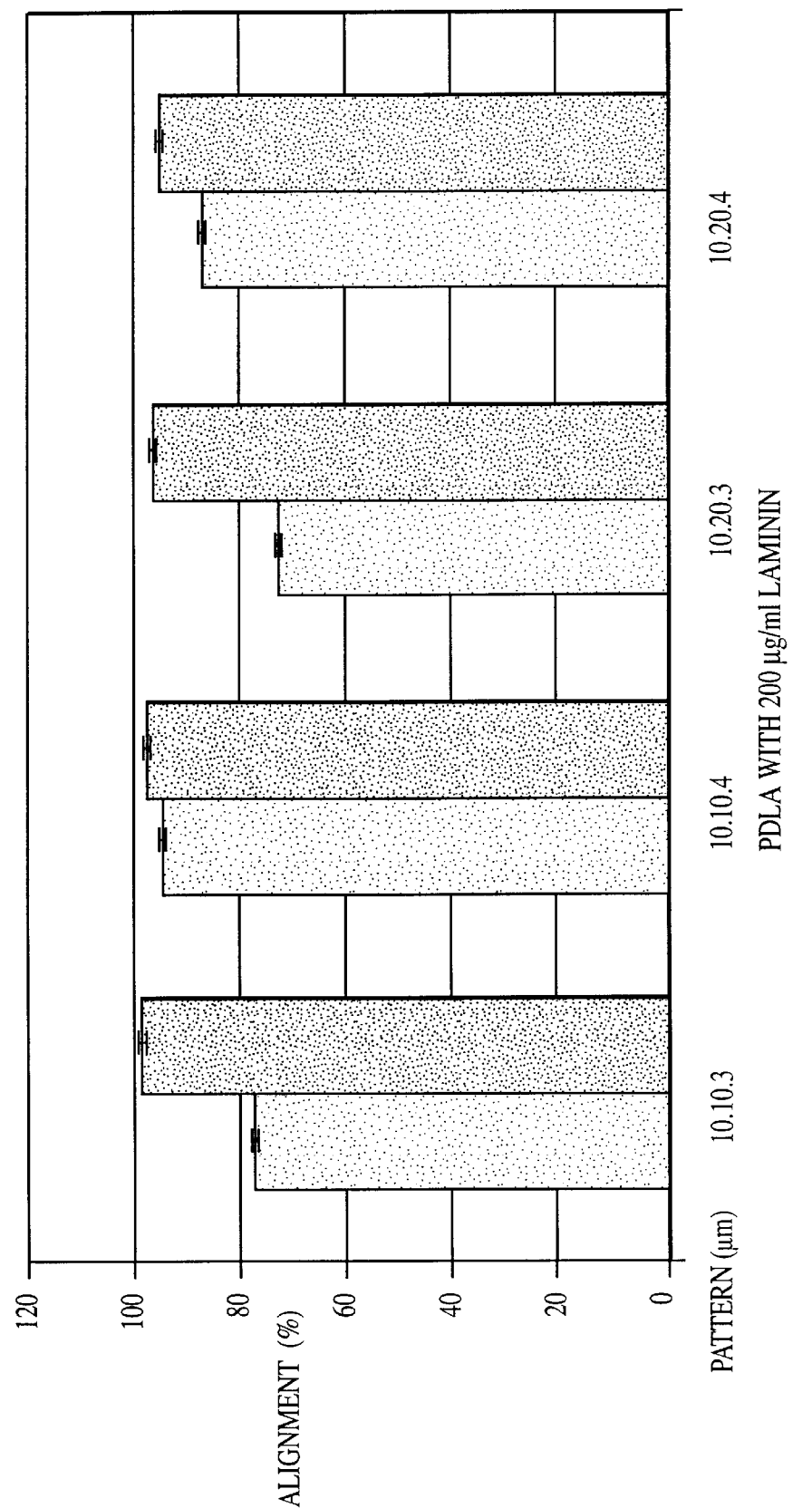
FIGS. 12 and 13 are charts illustrating the effects of Schwann cells, laminin, and micropatterned biodegradable polymers on neurite alignment and elongation.

[a]N = 18 and reported as standard error
[b]Aligned to chosen major axis
[c]Reported as standard error As shown in FIG. 12, grooves of 3 μm showed 25% improved alignment with the groove axis in PDLA substrates with 10.10.3 groove patterns and 35% improved alignment in PDLA substrates with 10.20.3 groove patterns. This improvement in alignment is important because as the groove depth decreases due to degradation, the Schwann cells provided guidance cues that maintain neurite alignment.

FIG. 13 shows the effects of seeding Schwann cells in grooves on nerve elongation in PDLA substrates with 200 μg/ml laminin having 10.10.4 and 10.20.4 groove patterns. Schwann cells improved elongation rates by approximately 75% in substrates with 10.10.4 groove patterns and by approximately 150% in substrates with 10.20.4 groove patterns. Seeding neurons on laminin coated Schwann cell seeded films improved neurite alignment at a 95% confidence level compared to the coated films without Schwann cells. Neurites seeded with Schwann cells aligned 95±2% on laminin (200 μg/ml) coated 10×10×4 μm PDLA while neurons seeded alone aligned 93±2%.

EXAMPLE 11

Qualitative Evaluation of Nerve Regeneration Following Implantation of Micropatterned Conduits The micropatterned films with laminin selectively adsorbed in the grooves are rolled and inserted into biodegradable porous PDLA conduits and injected with media containing Schwann cells. The conduits were prepared and given a number corresponding to the conduit type (seeded with Schwann cells and laminin and micropatterned with grooves=MS; unseeded and micropatterned=M; seeded with Schwann cells and nonmicropatterned=NS; and unseeded and nonmicropatterned=N). The sciatic nerves of 20 Sprague-Dawley rats were transected at mid-thigh and the conduit inserted at the site of a 1-cm transection and sutured.

Figure 4:
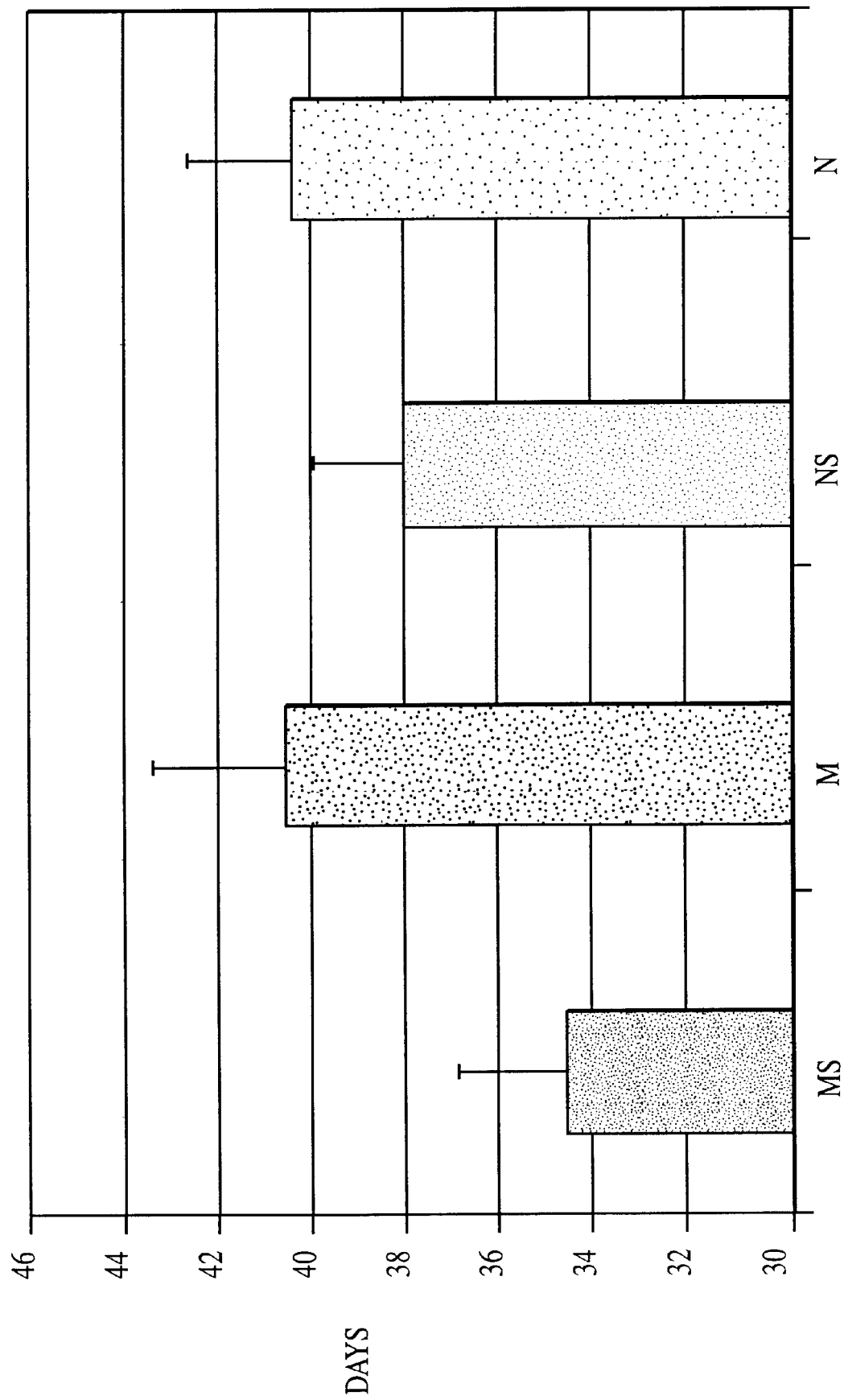
FIGS. 4–6 are charts illustrating the results of experiments showing qualitative improvement of nerve regeneration following implantation of guidance conduits containing micropatterned substrates in accordance with the invention.
Figure 5:
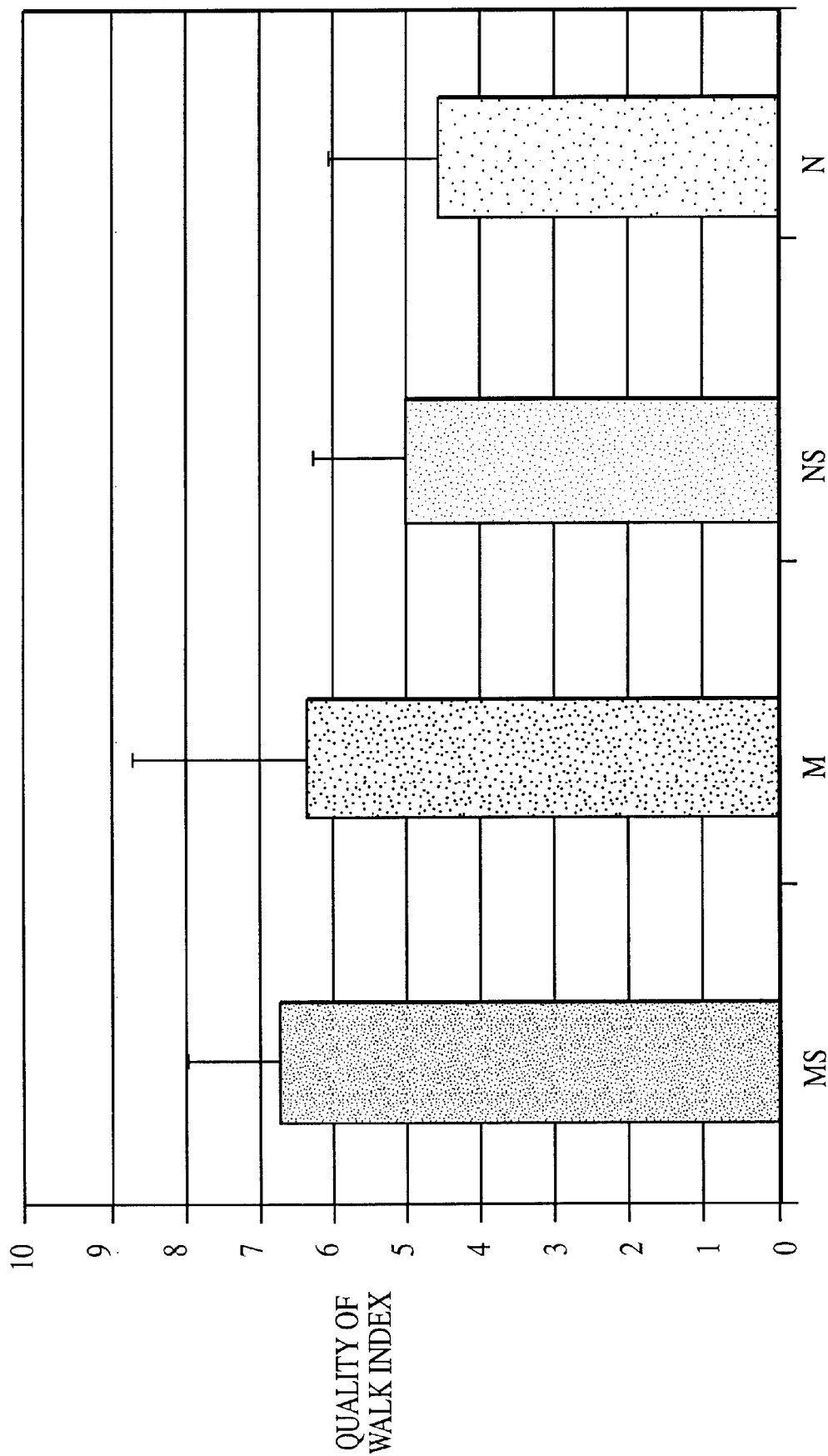
Figure 6:
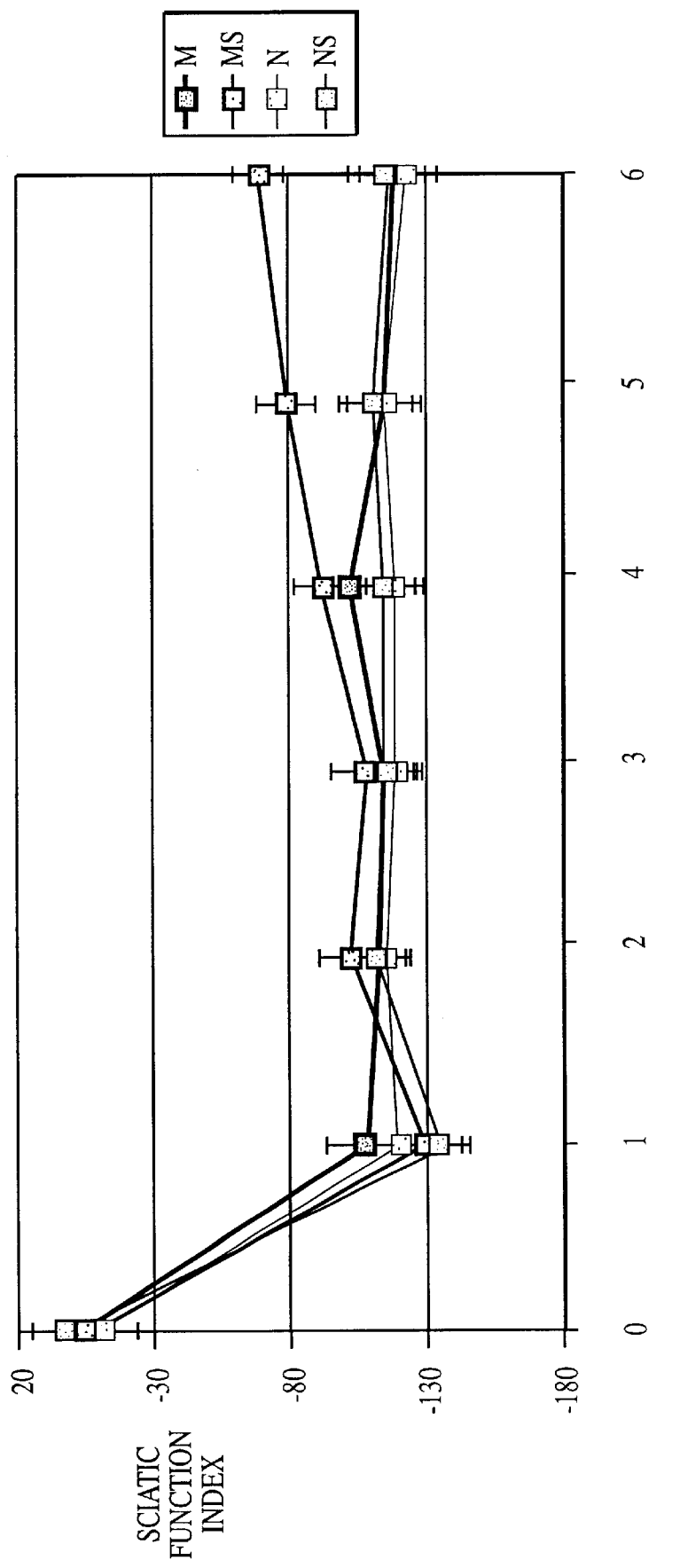

The animals were observed daily to check for signs of recovery as well as indications of automutilation. Toes were curled together immediately after surgery. The onset of toe spreading was noted as an indication of recovery from the nerve injury. The animals were examined and the end of the study for their ability to walk by observing toe spread and limping. The results of these experiments are shown in FIGS. 4–6. The micropatterned and seeded substrates (MS) showed the lowest level of toe spread (FIG. 4), highest level of walk quality (FIG. 5) and fastest sciatic nerve function recovery (FIG. 6).

Recovery from surgery was evaluated through the use of walking track analysis to determine a sciatic function index, SFI, of the test subjects. The rats were walked though a track set on plain white printing paper. The rats were trained to walk through the track before each trial. The hind paws of the rats were coated with block printing paint in order to leave tracks on the paper. The tracks were measured for toe spread, and intermediate toes spread in order to calculate SFI. Each rat was evaluated prior to surgery and weekly post surgery for the entire recovery period.

Over the length of the experiment, the rats were observed to look for signs of recovery from the nerve injury. After the initial surgical procedure, the toes curled up together. Also, the onset of toe spreading was noted as an indication of reinnervation of the muscle by the motor neurons. Walking track analysis was performed to quantitatively measure the recovery from the nerve injury. FIG. 4 summarizes the onset of toes spreading. The rats implanted with micropatterned conduits seeded with Schwann cells had an earlier onset of toes spreading. This correlated well with the increase in sciatic function index determined using walking track analysis as described below. Prior to removing the conduit, the rats were observed for their quality of walk giving consideration to toes spreading and limping. The results did not show any statistically significant differences among the various conduit types.

FIG. 4 is a chart illustrating observations of toe spread. Toe spreading was qualitatively evaluated. The time of onset was significantly lower for the animals receiving the micropatterned conduit seeded with Schwann cells (MS) compared with unseeded micropatterned (M), seeded nonmicropatterned (NS), and control (N). Error bars (in this and all presented graphs) represent 95% confidence intervals.

FIG. 5 is a chart illustrating qualitative walking ability of the rats before removal of the conduit. The quality of walk index is defined as follows: 1: no change over time of study, 2–4: slight toe spreading and severe limping, 5–7: moderate toe spreading and limping, 8–10: toes are fully spread, little sign of limping. Error bars represent 95% confidence intervals. As shown in FIG. 5, the quality of walk index for microfabricated and seeded substrates was approximately 30% higher than nonmicrofabricated and seeded substrates.

FIG. 6 is a chart of sciatic function determined using walking tract analysis. Improvement is observed after the fourth week for the animals with the Schwann cell seeded microfabricated conduit (MS—second darkest line) relative to the others (M-darkest line, NS-second lightest line, N-lightest line). Error bars represent 95% confidence intervals. As shown in FIG. 6, the animals implanted with micropatterned and seeded substrates had an approximately 60% higher sciatic function index measurement than the other substrate used in the study.

EXAMPLE 12

Electrode Array Fabrication

Indium tin oxide (ITO) is used to fabricate the electrode arrays for use in the nerve regeneration conduits. Silica glass is coated with sputtered ITO and etched in HCl solution forming the electrode pattern. Aluminum oxide is deposited as the passivation film. A thin layer of poly(methyl methacrylate) is spin-cast on the substrate and patterned by reactive ion etching. The electrodes are fabricated on silica glass substrates and coated with a layer of biodegradable polymer such as PDLA. Laminin is adsorbed at the bottom of the grooves and Schwann cells seeded on the surfaces prior to neuronal seeding. The use of electrical signals will promote and increase the regeneration rates of the neurons.

Monitoring of nerve regrowth in vivo is carried out using in-situ optical sensors embedded into the substrates. Miniature fiber optic channels is used to send light signals down to the nerve regrowth region, and a local, multi-diode photo-detector array built from a-Si was used to monitor the nerve regrowth in-situ. A computer will control the nerve stimulation cycle and monitored the generated optical signals.

For the in vitro work, a thin polyimide film substrate is formed by spinning the liquid precursor on a silicon wafer and then curing the polyimide at an elevated temperature. Ten centimeter diameter silicon wafers are used as substrates to make use of standard microelectronic processing equipment. A thin film of metal is deposited on the substrates, either by evaporation or sputtering. The metal is patterned with standard lithographic techniques involving reactive ion etching (RIE) to form an array of electrodes that provided the required electric fields and the necessary contact pads. RIE is a dry developed process with an etch rate of about 30 nm/minute and a resolution of about 1.5 $\mu$m. The metal electrodes are typically of the order of a few $\mu$m in width and the lengths are varied to enable contact of a single electrode with each microgroove. If greater resolution is required, focused ion beam radiation can have a resolution of a few nm. A separate recording electrode is fabricated in addition to the stimulating electrodes.

A biocompatible polymer film (e.g., polystyrene, polyimide, polyurethanes, or silicone) is deposited on top of the patterned metal, ensuring a dielectric layer. The film is patterned to an optimized grove configuration that provided the guidance for neuron growth, as described above. For this work, groove widths of 5 to 10 $\mu$m with depths of 2 to 5 $\mu$m can be used. The pitch of the grooves can be 10 $\mu$m. Windows to contact pads on the lower polyimide/metal layer are opened. The grooves are aligned lithographically over the electrode patterns in order to provide the desired electric fields.

If desired, the polyimide/metal/polymer structure can be lifted off the silicon substrate although the silicon provides a very stable structure for support. This demonstrates the capability to place multiple layers on the polyimide while still maintaining registration between layers. Initially, a series of substrates are made with several electrode configurations. This allows a rapid determination of which configuration is most desirable and also allows optimization of the electrode layout. It will be possible to test and measure growth rates under various conditions including field strengths, field orientation and whether constant fields, pulsed fields or alternating.

Separate electrodes are connected to individual grooves in order to provide independent signals to each neuron. Because of the close proximity of adjacent neurons, the electrodes are carefully laid out to avoid cross talk and activation of adjacent neurons. The multilayer configuration of the substrate will provide the flexibility to include shielding, if desired. In addition, the stimulating signal is of sufficiently low current density to a avoid irreversible reactions at the electrode—tissue interface. The design of the substrates allows for either capacitive or direct contact to the neurons as both have been demonstrated to impact growth.

REFERENCES

Akin T, Najafi K, Smoke R H, Bradley R M, *A Micromachined Silicon Sieve Electrode for Nerve Regeneration Applications,* IEEE Transactions On Biomedical Engineering 1994, 41, 305–313

Bunge, R. P., "Expanding Roles for the Schwann Cell: Ensheathment, Myelination, Trophism and Regeneration", *Curr. Biol.,* 3, 805–809 (1993).

Buettner, H. M., "Microcontrol of Neuronal Outgrowth", in *Nanofabrication and Biosystems: Integrating Materials Science, Engineering and Biology,* eds. Hoch, H. C., Jelinski, L. W., and Craighead, H. G., Cambridge University Press, Cambridge, UK, pp. 300–314, 1996.

Constant A, Burns S, Shanks H, Gruber C, Landin A, Schmidt D, Thielen C, Olympie F, Schumacher T, Cobbs J, *Development of Thin Film Transistor Based Circuits on Flexible Polyimide Substrates,* J. Electrochemical Society 2nd Symposium Proceedings, Y. Kuo Ed, 1994,94–35, 392.

den Dunnen W F A, Stokroos I, Blaauw E H, Holwerda A, Pennings A J, Robinson P H, Schakenraad J M, Light-microscopic and Electron-microscopic Evaluation of Short-term Nerve Regeneration Using a Biodegradable Poly(DL-lactide-□-caprolactone) Nerve Guide, J. Biomed. Mater. Res., 1996, 31, 105–115.

Dow, J. A., Clark, P., Connolly, P., Curtis, A. S. G., and Wilkinson, C. D. W., "Novel Methods for Guidance and Monitoring of Single Cell and Simple Networks in Culture", *J. Cell. Sci.,* 8, 55–79 (1987).

Fawcett, J., and Keynes, R., "Peripheral Nerve Regeneration", Ann. Rev. Neurosci., 13, 43–60 (1990).

Feneley, M. R., Fawcett, J. W., and Keynes, R. J., "The Role of Schwann Cells in Regeneration of Peripheral Nerve Axons Through Muscle Basal Lamina Grafts", *Exp. Neuro.,* 114, 275–285 (1991).

Mackinnon S E, Dennon A L, "Surgery of the Peripheral Nerve," Thieme Publishers, New York, N.Y., 1988.

Tai, H. C., and Buettner, H. M., "Neurite Outgrowth and Growth Cone Morphology on Micropatterned Surfaces", *Biotechnol. Prog.,* 14, 364–370 (1998).

Tessier-Lavigne, M., "Axon Guidance by Diffusible Repellants and Attractants", *Curr. Opin. Gene. and Dev.,* 4, 596–601 (1994).

Weiss, P., "Experiments of Cell and Axon Orientation Invitro: The Role of Colloidal Exudates in Tissue Organization", *J. Exp. Zool.,* 63, 401–450 (1945).

The above description and accompanying drawings are only illustrative of exemplary embodiments, which can achieve the features and advantages of the present invention. It is not intended that the invention be limited to the embodiments shown and described in detail herein. The invention can be modified to incorporate any number of variations, alterations, substitutions or equivalent arrangements not heretofore described, but which are commensurate with the spirit and scope of the invention. The invention is only limited by the scope of the following claims.

What is claimed as new and desired to be protected by Letters Patent of the United States is:

1. A method for regenerating a severed nerve, comprising:
   providing a substrate having a surface containing one or more substantially linear grooves;
   placing one or more guidance factors for nerve regeneration into said one or more grooves;
   wherein said one or more guidance factors comprises poly(vinyl alcohol);
   positioning said substrate in proximity to a severed end of said nerve such that said one or more grooves is substantially coextensive to said severed end; and allowing said severed nerve to grow into said one or more grooves of said substrate.

2. The method of claim 1 wherein said substrate is in the form of a cylinder.

3. The method of claim 2 wherein said cylindrical form has an inner and outer surface and said one or more grooves are disposed on said inner surface.

4. The method of claim 1 wherein said one or more guidance factors further comprise negative guidance factors disposed on said surface in between said one or more grooves.

5. The method of claim 1, wherein said substrate comprises a material selected from the group consisting of poly(D,L-lactide), lactic acid, glycolic acids, glycolide trimethylene carbonate, polyester, polyglycolic acid, collagen, polylactic acid, poly(organo)phosphazine, polyorthoester, glycosaminoglycan, L-lactide, ε-caprolactone, polyurethane, polyimides, and polystyrene.

6. The method of claim 1, wherein said substrate comprises poly(D,L-lactide).

7. The method of claim 1, wherein said substrate comprises copolymers of lactic and glycolic acids.

8. The method of claim 1, wherein said substrate further comprises at least one electrode.

9. The method of claim 8, wherein said at least one electrode is positioned within said one or more grooves.

10. The method of claim 1, wherein said one or more grooves are at least about 1 μm in width.

11. The method of claim 10, wherein said one or more grooves are up to about 50 μm in width.

12. The method of claim 1, wherein said one or more grooves are at least about 5 μm in width.

13. The method of claim 12, wherein said one or more grooves are up to about 10 μm in width.

14. The method of claim 1, wherein said one or more grooves are spaced at least about 10 μm apart.

15. The method of claim 14, wherein said one or more grooves are spaced up to about 20 μm apart.

16. The method of claim 14, wherein said one or more grooves are spaced up to about 100 μm apart.

17. The method of claim 1, wherein said one or more grooves are at least about 1 μm in depth.

18. The method of claim 17, wherein said one or more grooves are up to about 4 μm in depth.

19. The method of claim 1, wherein said one or more guidance factors comprises a material selected from the group consisting of Schwann cells, stem cells, nerve growth factor, laminin, collagen, polylysine, and chicken plasma.

20. The method of claim 1, wherein said one or more guidance factors comprises Schwann cells.

21. The method of claim 20, wherein said one or more guidance factors comprises stem cells.

22. The method of claim 21 wherein said stem cells are neuronal stem cells.

23. The method of claim 20, wherein said one or more guidance factors further comprises laminin.

24. The method of claim 23, wherein said one or more guidance factors further comprises stem cells.

25. The method of claim 24, wherein said stem cells are neuronal stem cells.

26. The method of claim 23 wherein neurite alignment of said severed nerve along said one or more grooves is at least about 90 percent.

27. The method of claim 1, wherein said one or more grooves contain Schwann cells at a concentration of at least about 50,000 cells/cm2.

28. The method of claim 27, wherein said one or more grooves contain Schwann cells at a concentration of up to about 400,000 cells/cm2.

29. The method of claim 1, wherein said one or more grooves contain laminin at a concentration of at least about 100 μg/ml.

30. The method of claim 29, wherein said one or more grooves contain laminin at a concentration of up to about 200 μg/ml.

31. The method of claim 1, wherein said severed nerve is part of the peripheral nervous system of a vertebrate.

32. The method of claim 1, wherein said severed nerve is part of the central nervous system of a vertebrate.

33. The method of claim 1, wherein said severed nerve is an optic nerve.

34. A method for regenerating a severed nerve, comprising:

providing a porous guidance conduit having an inner surface and an outer surface;

providing a substrate containing one or more substantially linear grooves, wherein said one or more grooves contain one or more guidance factors for nerve regeneration and wherein said substrate is disposed on the inner surface of said conduit;

positioning said guidance conduit in proximity to a severed end of said nerve; and allowing said severed nerve to grow into said grooves of said substrate.

35. The method of claim 34, wherein said guidance conduit is sutured to at least one end of said severed nerve.

36. A method for regenerating a severed nerve, comprising:

providing a substrate having a surface containing a plurality of substantially linear grooves, wherein said one or more grooves are substantially parallel and contain one or more guidance factors for nerve regeneration;

wherein said substrate comprises a material selected from the group consisting of poly(D,L-lactide), and copolymers of lactic and glycolic acids;

providing a porous guidance conduit having an inner surface wherein said substrate is disposed on the inner surface of said conduit;

attaching said guidance conduit between the severed ends of said nerve; and allowing said severed nerve to grow into said grooves of said substrate.

37. The method of claim 36 wherein said one or more guidance factors comprises a material selected from the group consisting of Schwann cells and laminin.

38. The method of claim 37 wherein said one or more grooves are at least about 5 μm wide, spaced at least about 10 μm apart, and are at least about 1 μm deep.

39. The method of claim 38 wherein said one or more grooves are no greater than about 10 μm wide, spaced no greater than about 100 μm apart, and are no greater than about 4 μm deep.

40. An apparatus for regenerating a severed nerve comprising:

a substrate having a surface containing one or more substantially linear grooves at least about 5 μm wide, spaced at least about 10 μm apart, and at least about 1 μm deep, wherein said one or more grooves contain one or more guidance factors for nerve regeneration, said guidance factors being selected from the group consisting of Schwann cells, stem cells, nerve growth factor, laminin, collagen, polylysine and chicken plasma; and one or more negative guidance factors comprising poly(vinyl alchohol).

41. The apparatus of claim 40 wherein said substrate is in the form of a cylinder.

42. The apparatus of claim 40 wherein said cylindrical form has an inner and an outer surface and said one or more grooves are disposed on said inner surface.

43. The apparatus of claim 40 wherein said one or more negative guidance factors are disposed in between said one or more grooves.

44. The apparatus of claim 40, wherein said substrate comprises a material selected from the group consisting of poly(D,L-lactide), lactic acid, glycolic acids, glycolide trimethylene carbonate, polyester, polyglycolic acid, collagen, polylactic acid, poly(organo)phosphazine, polyorthoester, glycosaminoglycan, L-lactide, ε-caprolactone, polyurethane, polyimides, and polystyrene.

45. The apparatus of claim 40, wherein said substrate comprises poly(D,L-lactide).

46. The apparatus of claim 40, wherein said substrate comprises copolymers of lactic and glycolic acids.

47. The apparatus of claim 40, wherein said substrate further comprises at least one electrode.

48. The apparatus of claim 47, wherein said electrode is positioned in said one or more grooves.

49. The apparatus of claim 40, wherein said one or more grooves are at least about 1 μm in width.

50. The apparatus of claim 49, wherein said one or more grooves are up to about 50 μm in width.

51. The apparatus of claim 40, wherein said one or more grooves are at least about 5 μm in width.

52. The apparatus of claim 51, wherein said one or more grooves are up to about 10 μm in width.

53. The apparatus of claim 40, wherein said one or more grooves are about 10 μm in width.

54. The apparatus of claim 40, wherein said one or more grooves are spaced at least about 10 μm apart.

55. The apparatus of claim 40, wherein said one or more grooves are spaced up to about 20 μm apart.

56. The apparatus of claim 55, wherein said one or more grooves are spaced up to about 100 μm apart.

57. The apparatus of claim 40, wherein said one or more grooves are at least about 1 μm in depth.

58. The apparatus of claim 57, wherein said one or more grooves are up to about 4 μm in depth.

59. The apparatus of claim 40, wherein said one or more guidance factors comprises Schwann cells.

60. The apparatus of claim 59, wherein said one or more guidance factors comprises stem cells.

61. The apparatus of claim 60, wherein said stem cells are neuronal stem cells.

62. The apparatus of claim 40, wherein said one or more guidance factors comprises laminin.

63. The apparatus of claim 62, wherein said one or more guidance factors further comprises stem cells.

64. The apparatus of claim 63, wherein said stem cells are neuronal stem cells.

65. The apparatus of claim 40, wherein said one or more grooves contain Schwann cells at a concentration of at least about 50,000 cells/cm2.

66. The apparatus of claim 40, wherein said one or more grooves contain Schwann cells at a concentration of up to about 400,000 cells/cm2.

67. The apparatus of claim 40, wherein said one or more grooves contain laminin at a concentration of at least about 100 μg/ml.

68. The apparatus of claim 40, wherein said one or more grooves contain laminin at a concentration of up to about 200 μg/ml.

69. An apparatus adapted for connection to at least one end of a severed nerve, comprising:
a cylindrical porous guidance conduit having an inner and an outer surface;
a substrate having a surface containing one or more substantially linear grooves, wherein said grooves contain one or more guidance factors for nerve regeneration; and
wherein said substrate is disposed on the inner surface of said guidance conduit.

70. An apparatus adapted for connection to at least one end of a severed nerve, comprising:
a cylindrical guidance conduit having an inner and an outer surface;
wherein said guidance conduit is sutured to at least one end of said severed nerve;
a substrate having a surface containing one or more substantially linear grooves, wherein said grooves contain one or more guidance factors for nerve regeneration; and
wherein said substrate is disposed on the inner surface of said guidance conduit.

71. An apparatus for regenerating a severed nerve, comprising:
a porous cylindrical guidance conduit having an inner and outer surface;
a substrate having a surface containing one or more substantially linear grooves, wherein said one or more grooves contain one or more guidance factors for nerve regeneration, said guidance factors being selected from the group consisting of Schwann cells, stem cells, nerve growth factor, laminin, collagen, polylysine and chicken plasma; and
wherein said substrate is disposed on the inner surface of said guidance conduit.

72. The apparatus of claim 71, wherein said substrate comprises a material selected from group consisting of poly(D,L-lactide) or copolymers of lactic and glycolic acids.

73. The apparatus of claim 72, wherein said one or more guidance factors comprises a material selected from the group consisting of Schwann cells and laminin.

74. The apparatus of claim 71 wherein said one or more grooves are at least about 5 μm wide, spaced at least about 10 μm apart, and are at least about 1 μm deep.

75. The apparatus of claim 74 wherein said one or more grooves are no greater than about 10 μm wide, spaced no greater than about 100 μm apart, and are no greater than about 4 μm deep.

* * * * *

UNITED STATES PATENT AND TRADEMARK OFFICE
CERTIFICATE OF CORRECTION

PATENT NO. : 6,676,675 B2
DATED : January 13, 2004
INVENTOR(S) : Surya K. Mallapragada et al.

It is certified that error appears in the above-identified patent and that said Letters Patent is hereby corrected as shown below:

Column 6,
Line 65, "micropaterned" should read -- micropatterned --.

Column 7,
Line 22, "is" should read -- are --.

Column 9,
Line 9, delete "is".

Column 17,
Line 64, "to a avoid" should read -- to avoid --.

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,676,675 B2
DATED : January 13, 2004
INVENTOR(S) : Surya K. Mallapragada et al.

It is certified that error appears in the above-identified patent and that said Letters Patent is hereby corrected as shown below:

Title page,
Item [56], References Cited, OTHER PUBLICATIONS, should read
-- Britland, et al "Embryonic Xenopus neurites integrate and respond to simultaneous electrical and adhesive guidance cues," Experimental Cell Research, 1996, vol. 225, pp. 31-38. --

Signed and Sealed this

Tenth Day of August, 2004

JON W. DUDAS
*Acting Director of the United States Patent and Trademark Office*